(12) United States Patent
Kawada et al.

(10) Patent No.: US 12,426,503 B2
(45) Date of Patent: Sep. 23, 2025

(54) MATERIAL FOR PHOTOELECTRIC CONVERSION ELEMENT FOR IMAGING

(71) Applicant: NIPPON STEEL Chemical & Material Co., Ltd., Tokyo (JP)

(72) Inventors: Atsushi Kawada, Tokyo (JP); Munetomo Inoue, Tokyo (JP); Kentaro Hayashi, Tokyo (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 374 days.

(21) Appl. No.: 18/031,956

(22) PCT Filed: Nov. 25, 2021

(86) PCT No.: PCT/JP2021/043224
§ 371 (c)(1),
(2) Date: Apr. 14, 2023

(87) PCT Pub. No.: WO2022/114067
PCT Pub. Date: Jun. 2, 2022

(65) Prior Publication Data
US 2023/0389419 A1 Nov. 30, 2023

(30) Foreign Application Priority Data
Nov. 27, 2020 (JP) .................. 2020-196818

(51) Int. Cl.
*H10K 85/60* (2023.01)
*C07D 487/04* (2006.01)
(Continued)

(52) U.S. Cl.
CPC ....... *H10K 85/6572* (2023.02); *C07D 487/04* (2013.01); *H10K 85/654* (2023.02); *H10K 30/85* (2023.02); *H10K 30/86* (2023.02)

(58) Field of Classification Search
None
See application file for complete search history.

(56) References Cited

U.S. PATENT DOCUMENTS

| 2017/0309849 A1 | 10/2017 | Umehara et al. |
| 2018/0151625 A1 | 5/2018 | Hasegawa et al. |

(Continued)

FOREIGN PATENT DOCUMENTS

| JP | 2018-85427 A | 5/2018 |
| JP | 2019-54228 A | 4/2019 |

(Continued)

OTHER PUBLICATIONS

Aihara et al., "Research trends in organic imaging devices", NHK Science & Technology Research Laboratories R & D, No. 132, 2012.3, pp. 4-11.

(Continued)

*Primary Examiner* — Anthony Ho
(74) *Attorney, Agent, or Firm* — Birch, Stewart, Kolasch & Birch, LLP

(57) ABSTRACT

Provided are a material that achieves higher sensitivity and higher resolution of a photoelectric conversion element for imaging, and a photoelectric conversion element for imaging using the above material. A material for a photoelectric conversion element for imaging, the material having a structure of the following general formula (1), wherein L each independently represents a single bond, an aromatic hydrocarbon group having 6 to 30 carbon atoms, or the like; "a" represents the number of substitutions, and represents an integer of 1 to 6; $Ar^1$ each independently represents a group represented by the following formula (2); and $Ar^2$ each independently represents an aromatic heterocyclic group having 3 to 30 carbon atoms and containing a nitrogen- (Continued)

containing six-membered cyclic structure, or the like, provided that a group bonded to L is the aromatic heterocyclic group. The ring B represents a heterocyclic ring represented by the formula (2a) and fused with an adjacent ring at any position; "*" in the formula (2) represents a bonding position to L in the formula (1); and X represents O, S, or N—Ar³.

$(Ar^1\text{—}L\text{)}_a\text{—}Ar^2$ (1)

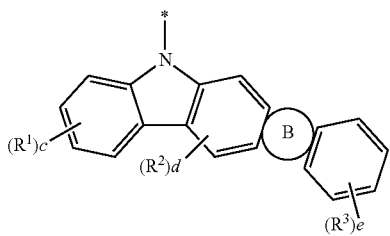

(2)

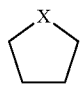

(2a)

13 Claims, 1 Drawing Sheet

(51) Int. Cl.
*H10K 30/85* (2023.01)
*H10K 30/86* (2023.01)

(56) References Cited

U.S. PATENT DOCUMENTS

| | | |
|---|---|---|
| 2019/0115544 A1 | 4/2019 | Zink et al. |
| 2019/0288040 A1 | 9/2019 | Ujiie et al. |
| 2021/0119149 A1 | 4/2021 | Negishi et al. |

FOREIGN PATENT DOCUMENTS

| | | |
|---|---|---|
| JP | 2019-57704 A | 4/2019 |
| KR | 10-2018-0015132 A | 2/2018 |
| WO | WO 2014/156771 A1 | 10/2014 |
| WO | WO 2016/111140 A1 | 7/2016 |

OTHER PUBLICATIONS

Namba et al., "Photoelectric conversion film laminated type: Technological trends in imaging devices", NHK Science & Technology Research Laboratories R & D, No. 174, 2019.3, pp. 4-17.

Togashi et al., "Three-layer Stacked Color Image Sensor With 2.0-μm Pixel Size Using Organic Photoconductive Film", IEEE International Electron Devices Meeting (IEDM), 2019, pp. 16.6.1-16.6.4.

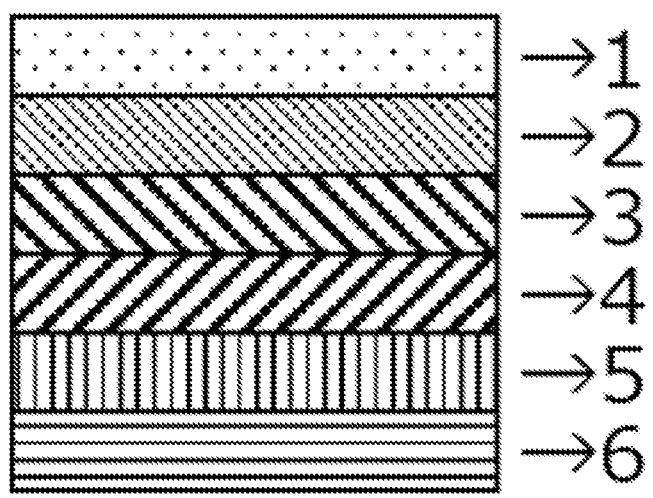

MATERIAL FOR PHOTOELECTRIC CONVERSION ELEMENT FOR IMAGING

TECHNICAL FIELD

The present invention relates to a material for a photoelectric conversion element and a photoelectric conversion element using the same, and particularly to a material for a photoelectric conversion element useful for an imaging device.

In recent years, development of an organic electronic device using a thin film formed with an organic semiconductor (also referred to as an organic charge transport material) is in progress. Examples thereof include an electroluminescent element, a solar cell, a transistor element, and a photoelectric conversion element. In particular, development of an organic EL element, which is an electroluminescent element with an organic substance, is most advanced among them. The applications for smartphones, TV and the like are in progress, and development for a purpose of further higher functionality is continuously conducted.

On the photoelectric conversion element, an element using a P-N junction of an inorganic semiconductor, such as silicon, has been conventionally developed and practically used, and made are investigations for high functionalization of a digital camera and a camera for a smartphone and investigation for application for a monitoring camera, a sensor for an automobile, and the like. However, problems for these various uses include improving sensitivity and micronizing a pixel (improving resolution). For the photoelectric conversion element using an inorganic semiconductor, a mainly adopted method for obtaining a color image is disposing color filters corresponding to RGB, which are the three primary colors of light, on a light receiving part of the photoelectric conversion element. This method has problems in terms of utilization efficiency of an incident light and resolution, because the method disposes the RGB color filters on a plane (Non Patent Literature 1 and 2).

As a solution for such problems of the photoelectric conversion element, a photoelectric conversion element using an organic semiconductor instead of the inorganic semiconductor is developed (Non Patent Literature 1 and 2). This utilizes "an ability to selectively absorb only light having a specific wavelength region with high sensitivity" that the organic semiconductor has, and proposed is stacking photoelectric conversion elements composed of organic semiconductors corresponding to the three primary colors of light to solve the problem of improving the sensitivity and improving the resolution. An element in which a photoelectric conversion element composed of the organic semiconductor and a photoelectric conversion element composed of the inorganic semiconductor are stacked is also proposed (Non Patent Literature 3).

Here, the photoelectric conversion element composed of the organic semiconductor is an element having a photoelectric conversion layer composed of a thin film of the organic semiconductor between two electrodes, wherein a hole blocking layer and/or an electron blocking layer is disposed between the photoelectric conversion layer and the two electrodes, as necessary. In the photoelectric conversion element, light having a desired wavelength is absorbed in the photoelectric conversion layer to generate an exciter, and then charge separation of the exciter generates a hole and an electron. Thereafter, the hole and the electron move toward each electrode to convert the light into an electric signal. For a purpose of accelerating this process, a method of applying a bias voltage between both the electrodes is commonly used, but one of objects is reducing a leakage current from both the electrodes generated by applying the bias voltage. Accordingly, it can be mentioned that controlling the move of the hole and the electron in the photoelectric conversion element is a key to exhibit characteristic of the photoelectric conversion element.

The organic semiconductor used for each layer of the photoelectric conversion element can be classified into a P-type organic semiconductor and an N-type organic semiconductor. The P-type organic semiconductor is used as a hole transport material, and the N-type organic semiconductor is used as an electron transport material. To control the move of the hole and the electron in the aforementioned photoelectric conversion element, made are various developments of an organic semiconductor having appropriate physical properties such as hole mobility, electron mobility, an energy value of a highest occupied molecular orbital (HOMO), and an energy value of a lowest unoccupied molecular orbital (LUNO). However, the organic semiconductor still has insufficient characteristics, and has not been utilized in commercial practice.

Patent literature 1 proposes an element using quinacridone as the P-type organic semiconductor and subphthalocyanine chloride as the N-type organic semiconductor for the photoelectric conversion layer, and an indolocarbazole derivative for a first buffer layer (which has presumably the same means as the electron blocking layer) disposed between the photoelectric conversion layer and the electrode. The application of the indolocarbazole derivative therein is limited to the first buffer layer, and applicability for the photoelectric conversion layer is unknown.

Patent literature 2 proposes an element using, for the photoelectric conversion layer, a chrysenodithiophene derivative as the P-type organic semiconductor and fullerenes or a subphthalocyanine derivative as the N-type organic semiconductor.

Patent literature 3 proposes an element using a benzodifuran derivative for the electron blocking layer disposed between the photoelectric conversion layer and the electrode.

Patent literature 4 proposes an element containing, for the photoelectric conversion layer, a hydrocarbon-based fused aromatic derivative having an electron donating group as the P-type organic semiconductor and a hydrocarbon-based fused aromatic derivative having an electron withdrawing group as the N-type organic semiconductor.

CITATION LIST

Patent Literature

Patent Literature 1

JP 2018-85427 (A)

Patent Literature 2

JP 2019-54228 (A)

Patent Literature 3

JP 2019-57704 (A)

Patent Literature 4

International Publication No. WO 2016-111140

Non Patent Literature

Non Patent Literature 1

NHK Science & Technology Research Laboratories R& D No. 132, pp. 4-11 (2012.3)

Non Patent Literature 2

NHK Science & Technology Research Laboratories R& D No. 174, pp. 4-17 (2019.3)

Non Patent Literature 3

2019 IEEE International Electron Devices Meeting (IEDM), pp. 16.6.1-16.6.4 (2019)

SUMMARY OF INVENTION

In the use of the photoelectric conversion element for imaging for highly functionalizing a digital camera and a camera for a smartphone and for application for a monitoring camera, a sensor for an automobile, and the like, challenges are further higher sensitivity and higher resolution. In view od such a circumstance, an object of the present invention is to provide a material that achieves higher sensitivity and higher resolution of the photoelectric conversion element for imaging, and a photoelectric conversion element for imaging using the same.

The present inventors have made intensive investigation, and consequently found that using a compound represented by the formula (1) efficiently proceeds a process of generating a hole and an electron by charge separation of an exciter in a photoelectric conversion layer, and a process of moving of the hole and the electron in the photoelectric conversion element. The finding has led to the completion of the present invention.

The present invention is a material for a photoelectric conversion element for imaging, the material being a compound having a structure of the following general formula (1):

[C 1]

wherein L each independently represents a single bond, a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, or a substituted or unsubstituted linked aromatic group in which two to six of any one or more of the aromatic hydrocarbon group or the aromatic heterocyclic group are linked;

"a" represents the number of substitutions, and represents an integer of 1 to 6;

$Ar^1$ each independently represents a group represented by the following formula (2); and $Ar^2$ each independently represents a substituted or unsubstituted aromatic heterocyclic group having 3 to 30 carbon atoms and containing a nitrogen-containing six-membered cyclic structure, or a substituted or unsubstituted linked aromatic group which contains at least one of the aromatic heterocyclic group and in which two to seven of any one or more of the aromatic heterocyclic group or an aromatic hydrocarbon group having 6 to 30 carbon atoms are linked, provided that a group bonded to L is the aromatic heterocyclic group,

[C 2]

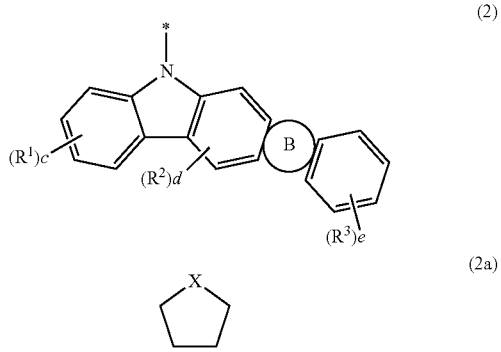

wherein ring B represents a heterocyclic ring represented by the formula (2a) and fused with an adjacent ring at any position; "*" in the formula (2) represents a bonding position to L in the formula (1); and X represents O, S, or N—$Ar^3$;

$Ar^3$ each independently represents a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, a substituted or unsubstituted linked aromatic group in which two to six of any one or more of the aromatic hydrocarbon group or the aromatic heterocyclic group are linked, or L-$Ar^2$;

$R^1$, $R^2$, and $R^3$ represent a substituent, and each independently represent an alkyl group having 1 to 20 carbon atoms, an alkenyl group having 1 to 20 carbon atoms, a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, or a substituted or unsubstituted linked aromatic group in which two to six of any one or more of the aromatic hydrocarbon group or the aromatic heterocyclic group are linked; and $R^1$, $R^2$, and $R^3$ are optionally bonded to any adjacent substituent to form a ring or form a fused ring with an adjacent ring; and "c" represents an integer of 0 to 4, "d" represents an integer of 0 to 2, and "e" represents an integer of 0 to 4.

Here, $Ar^2$ preferably contains at least one substituted or unsubstituted azine skeleton, further preferably contains at least one substituted or unsubstituted pyridine, pyrimidine, or triazine skeleton, and more preferably contains at least one substituted or unsubstituted triazine skeleton.

In the material for a photoelectric conversion element, an energy level of highest occupied molecular orbital (HOMO) obtained by structural optimization calculation with a density functional calculation B3LYP/6-31G(d) is preferably −4.5 eV or lower, or an energy level of lowest unoccupied molecular orbital (LUMO) is preferably −2.5 eV or higher.

The material for a photoelectric conversion element preferably has a hole mobility of $1\times10^{-6}$ $cm^2/Vs$ or more, or is preferably amorphous.

In the aromatic heterocyclic group having 4 to 30 carbon atoms and containing a five-membered heterocyclic structure used in L, substituent in $Ar^2$, $Ar^3$, substituents in $Ar^3$, $R^1$, $R^2$, and $R^3$ in the material for a photoelectric conversion element, the five-membered heterocyclic structure is preferably a pyrrole ring, a furan ring, or a thiophene ring.

The material for a photoelectric conversion element may be used as a hole transport material.

The present invention is a photoelectric conversion element for imaging, comprising a photoelectric conversion layer and an electron blocking layer between two electrodes, wherein at least one layer of the photoelectric conversion layer or the electron blocking layer contains the above material for a photoelectric conversion element.

In the photoelectric conversion element of the present invention, the photoelectric conversion layer may contain an electron transport material, and the electron blocking layer may contain the above material for a photoelectric conversion element.

Using the material for a photoelectric conversion element for imaging of the present invention can achieve appropriate move of the hole and the electron in the photoelectric conversion element, and consequently enables to reduce a leakage current generated by applying a bias voltage during the conversion of light into electric energy. As a result, a photoelectric conversion element that achieves a low dark current value and a high contrast ratio can be obtained.

Therefore, the above material is useful as a material for a photoelectric conversion element for a photoelectric-converting film-stacked imaging device.

BRIEF DESCRIPTION OF DRAWING

FIG. 1 is a sectional schematic view illustrating a structure example of a photoelectric conversion element used in the present invention.

DESCRIPTION OF EMBODIMENTS

The photoelectric conversion element for imaging of the present invention is a photoelectric conversion element having at least one organic layer between two electrodes and converting light into electric energy. The organic layer contains a material for a photoelectric conversion element for imaging represented by the general formula (1). As necessary, the organic layer containing the material for a photoelectric conversion element for imaging represented by the general formula (1) may be a plurality of the layers.

The compound represented by the general formula (1) will be described below.

L as a linking group each independently represents a single bond, a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, or a substituted or unsubstituted linked aromatic group in which two to six of any one or more of the aromatic hydrocarbon group or the aromatic heterocyclic group are linked. Preferably usable is a single bond, a substituted or unsubstituted aromatic hydrocarbon group having 6 to 20 carbon atoms, an aromatic heterocyclic group having 4 to 20 carbon atoms and containing a five-membered heterocyclic structure having at least one nitrogen, sulfur, or oxygen, or a substituted or unsubstituted linked aromatic group formed by linking of two to four aromatic groups selected from the aromatic hydrocarbon group and the aromatic heterocyclic group. Further preferably usable is a single bond, a substituted or unsubstituted aromatic hydrocarbon group having 6 to 18 carbon atoms, an aromatic heterocyclic group having 4 to 12 carbon atoms and containing a pyrrole ring, a furan ring, or a thiophene ring as the five-membered heterocyclic structure, or a substituted or unsubstituted linked aromatic group formed by linking of two to four aromatic groups selected from the aromatic hydrocarbon group or the aromatic heterocyclic group.

As the hydrocarbon aromatic group of L having 6 to carbon atoms, groups obtained by removing two hydrogens from known aromatic hydrocarbons can be used. For example, usable are: monocyclic aromatic hydrocarbons, such as benzene; bicyclic aromatic hydrocarbons, such as naphthalene; tricyclic aromatic hydrocarbons, such as indacene, biphenylene, phenalene, anthracene, phenanthrene, and fluorene; tetracyclic aromatic hydrocarbons, such as fluoranthene, acephenanthrylene, aceanthrylene, triphenylene, pyrene, chrysene, tetraphene, tetracene, and pleiadene; pentacyclic aromatic hydrocarbons, such as picene, perylene, pentaphene, pentacene, tetraphenylene, and naphthoanthracene; and the like. The hydrocarbon aromatic group is preferably benzene, naphthalene, anthracene, or triphenylene.

In the aromatic heterocyclic group of L having 4 to carbon atoms and containing the five-membered heterocyclic structure, the five-membered heterocyclic structure is preferably one obtained by removing two hydrogens from a known five-membered heterocyclic structure. Preferably usable are a pyrrole ring, a furan ring, and a thiophene ring. The aromatic heterocyclic group is preferably a group obtained by removing two hydrogens from an aromatic heterocyclic group having 4 to 30 carbon atoms and containing the five-membered heterocyclic structure formed by these rings. Examples thereof include: nitrogen-containing aromatic groups having a pyrrole ring, such as pyrrole, pyrrolopyrrole, indole, pyrroloindole, benzoindole, naphthopyrrole, isoindole, pyrroloisoindole, benzoisoindole, naphthoisopyrrole, carbazole, benzocarbazole, indoloindole, carbazolocarbazole, and carboline; sulfur-containing aromatic groups having a thiophene ring, such as thiophene, benzothiophene, naphthothiophene, dibenzothiophene, benzothienonaphthalene, benzothienobenzothiophene, benzothienodibenzothiophene, dinaphthothiophene, dinaphthothienothiophene, and naphthobenzothiophene; and oxygen-containing aromatic groups having a furan ring, such as furan, benzofuran, naphthofuran, dibenzofuran, benzofuronaphthalene, benzofurobenzofuran, benzofurodibenzofuran, dinaphthofuran, dinaphthofuranofuran, and naphthobenzofuran.

Here, the aromatic heterocyclic group of L containing the five-membered heterocyclic structure may be a structure in which a five-membered heterocyclic ring such as a pyrrole ring, a furan ring, and a thiophen ring is singly present, or may be a structure in which such a five-membered heterocyclic ring is fused with an aromatic ring such as a benzene ring and a carbazole ring.

The above group can be a group in which rings of two or more kinds of groups selected from the nitrogen-containing aromatic group, the sulfur-containing aromatic ring, the oxygen-containing aromatic group, and the like are fused. Examples of such a fused group include: groups in which an aromatic group having a pyrrole ring and an aromatic group having a furan ring are fused, such as benzofurobenzothiophene and benzofurobenzocarbazole; groups in which an aromatic group having a pyrrole ring and an aromatic group having a thiophene ring are fused, such as benzothienocarbazole and benzothienobenzocarbazole; and groups in which an aromatic group having a furan ring and an aromatic group having a thiophene ring are fused, such as benzofurodibenzothiophene and benzofurobenzocarbazole.

More preferable examples of the aromatic heterocyclic group of L containing the five-membered heterocyclic structure include: carbazole, benzocarbazole, indoloindole, and carbazolocarbazole, as the nitrogen-containing aromatic group having a pyrrole ring; thiophene, dibenzothiophene, benzothienonapthalene, benzothienobenzothiopene, benzothienodibenzothiophene, dinaphthothiophene, dinaphthothienothiophene, and naphthobenzothiophene, as the sulfur-containing aromatic group having a thiophene ring; and dibenzofuran, benzofuronaphthalene, benzofurobenzofuran, benzofurodibenzofuran, dinaphthofuran, dinaphthofuranofuran, and naphthobenzofuran, as the oxygen-containing aromatic group having a furan ring.

L may have a substituent, and examples of the substituent include an alkyl group having 1 to 20 carbon atoms. The alkyl group having 1 to 20 carbon atoms may be any of linear, branched, and cyclic alkyl groups, and is preferably a linear, branched, or cyclic alkyl group having 1 to 10 carbon atoms. Specific examples thereof include: linear saturated hydrocarbon groups, such as a methyl group, an ethyl group, a n-propyl group, a n-butyl group, a n-pentyl group, a n-hexyl group, a n-octyl group, a n-dodecyl group, a n-tetradecyl group, and a n-octadecyl group; branched saturated hydrocarbon groups, such as an isopropyl group, an isobutyl group, a neopentyl group, a 2-ethylhexyl group, and a 2-hexyloctyl group; and saturated alicyclic hydrocarbon groups, such as a cyclopentyl group, a cyclohexyl group, a cyclooctyl group, a 4-butylcyclohexyl group, and a 4-dodecylcyclohexyl group.

In the general formula (1), $Ar^2$ each independently represents a group represented by the formula (2). The ring B in the formula (2) represents a heterocyclic ring represented by the formula (2a) and fused with an adjacent ring at any position.

[C 3]

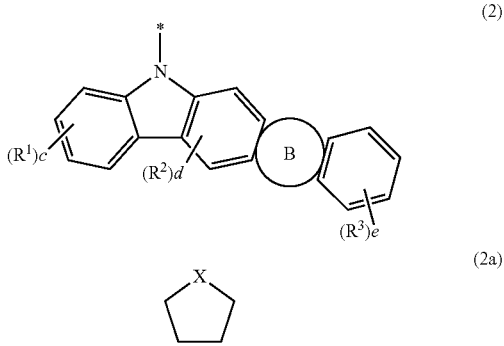

(2)

(2a)

In the formula (2a), X represents O, S, or N—$Ar^3$, and preferably N—$Ar^3$.

$Ar^3$ each independently represents a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, a linked aromatic group in which two to six of any one or more of the aromatic hydrocarbon group or the aromatic heterocyclic group are linked, or L-$Ar^2$.

$Ar^3$ is preferably a substituted or unsubstituted aromatic hydrocarbon group having 6 to 20 carbon atoms, an aromatic heterocyclic group having 4 to 20 carbon atoms and containing a five-membered heterocyclic structure, or a substituted or unsubstituted linked aromatic group formed by linking of two to four aromatic groups selected from the aromatic hydrocarbon group and the aromatic heterocyclic group.

$Ar^3$ is further preferably a substituted or unsubstituted aromatic hydrocarbon group having 6 to 18 carbon atoms, an aromatic heterocyclic group having 4 to 12 carbon atoms and containing a pyrrole ring, a furan ring, or a thiophene ring as the five-membered heterocyclic structure, or a substituted or unsubstituted linked aromatic group formed by linking of two to four aromatic groups selected from the aromatic hydrocarbon group or the aromatic heterocyclic group.

The aromatic hydrocarbon group of $Ar^3$ having 6 to 30 carbon atoms is preferably one obtained by removing one hydrogen from known aromatic hydrocarbons. Examples thereof include: monocyclic aromatic hydrocarbons, such as benzene; bicyclic aromatic hydrocarbons, such as naphthalene; tricyclic aromatic hydrocarbons, such as indacene, biphenylene, phenalene, anthracene, phenanthrene, and fluorene; tetracyclic aromatic hydrocarbons, such as fluoranthene, acephenanthrylene, aceanthrylene, triphenylene, pyrene, chrysene, tetraphene, tetracene, and pleiadene; pentacyclic aromatic hydrocarbons, such as picene, perylene, pentaphene, pentacene, tetraphenylene, and naphthoanthracene; and the like. The aromatic hydrocarbon group is preferably benzene, naphthalene, anthracene, or triphenylene.

In the aromatic heterocyclic group of $Ar^3$ having 4 to 30 carbon atoms and containing the five-membered heterocyclic structure, the five-membered heterocyclic structure is preferably one obtained by removing two hydrogens from a known five-membered heterocyclic structure. The five-membered heterocyclic structure is preferably a pyrrole ring, a furan ring, or a thiophene ring. The aromatic heterocyclic group is preferably one obtained by removing one hydrogen from an aromatic heterocyclic group having 4 to 30 carbon atoms and containing these five-membered heterocyclic structures. Examples thereof include: nitrogen-containing aromatic groups having a pyrrole ring, such as pyrrole, pyrrolopyrrole, indole, pyrroloindole, benzoindole, naphthopyrrole, isoindole, pyrroloisoindole, benzoisoindole, naphthoisopyrrole, carbazole, benzocarbazole, indoloindole, carbazolocarbazole, and carboline; sulfur-containing aromatic groups having a thiophene ring, such as thiophene, benzothiophene, naphthothiophene, dibenzothiophene, benzothienonapthalene, benzothienobenzothiopene, benzothienodibenzothiophene, dinaphthothiophene, dinaphthothienothiophene, and naphthobenzothiophene; and oxygen-containing aromatic groups having a furan ring, such as furan, benzofuran, naphthofuran, dibenzofuran, benzofuronaphthalene, benzofurobenzofuran, benzofurodibenzofuran, dinaphthofuran, dinaphthofuranofuran, and naphthobenzofuran.

More preferable examples of the aromatic heterocyclic group of $Ar^3$ having 4 to 30 carbon atoms and containing the five-membered heterocyclic structure include: carbazole, benzocarbazole, indoloindole, and carbazolocarbazole, as the nitrogen-containing aromatic group having a pyrrole ring; thiophene, dibenzothiophene, benzothienonaphthalene, benzothienobenzothiophene, benzothienodibenzothiophene, dinaphthothiophene, dinaphthothienothiophene, and naphthobenzothiophene, as the sulfur-containing aromatic group having a thiophene ring; and dibenzofuran, benzofuronaphthalene, benzofurobenzofuran, benzofurodibenzofuran, dinaphthofuran, dinaphthofuranofuran, and naphthobenzofuran, as the oxygen-containing aromatic group having a furan ring.

Ar³ may have a substituent, and examples of the substituent include an alkyl group having 1 to 20 carbon atoms. The alkyl group having 1 to 20 carbon atoms may be any of linear, branched, and cyclic alkyl groups, and is preferably a linear, branched, or cyclic alkyl group having 1 to 10 carbon atoms. Specific examples thereof include: linear saturated hydrocarbon groups, such as a methyl group, an ethyl group, a n-propyl group, a n-butyl group, a n-pentyl group, a n-hexyl group, a n-octyl group, a n-dodecyl group, a n-tetradecyl group, and a n-octadecyl group; branched saturated hydrocarbon groups, such as an isopropyl group, an isobutyl group, a neopentyl group, a 2-ethylhexyl group, and a 2-hexyloctyl group; and saturated alicyclic hydrocarbon groups, such as a cyclopentyl group, a cyclohexyl group, a cyclooctyl group, a 4-butylcyclohexyl group, and a 4-dodecylcyclohexyl group.

When X is N—Ar³ in the formula (2a), the five-membered fused ring represented by the general formula (2) represents an indolocarbazole skeleton, which has six isomers represented by the following formulae (U), (V), (W), (X), (Y), and (Z). The indolocarbazole skeleton is preferably the formula (U), (V), (W), or (Y). Note that, when X is O or S, there are also isomers similar to the indolocarbazole skeleton.

[C 4]

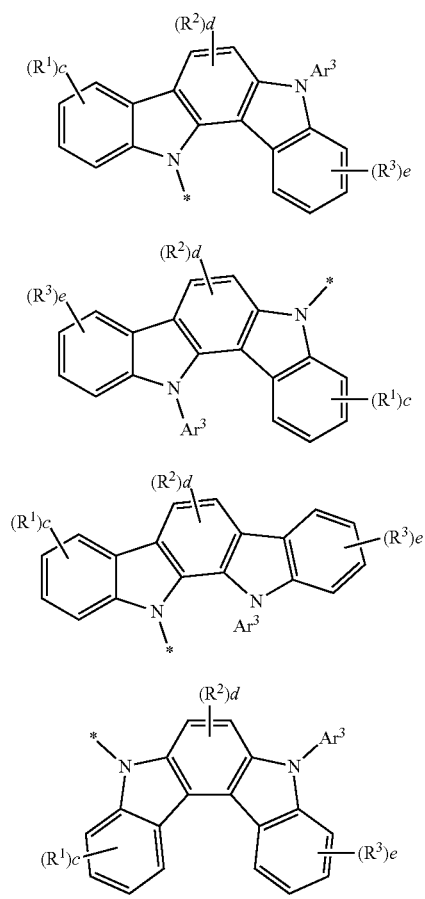

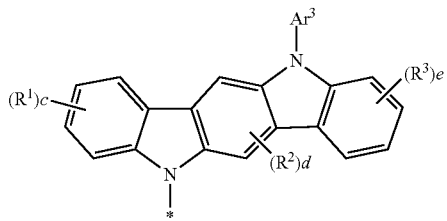

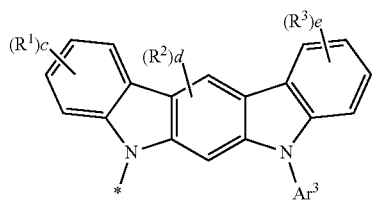

In the formula (2), $R^1$, $R^2$, and $R^3$ represent a substituent, and represents an alkyl group having 1 to 20 carbon atoms, an alkenyl group having 1 to 20 carbon atoms, a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, or a substituted or unsubstituted linked aromatic group in which two to six of any one or more of the aromatic hydrocarbon group or the aromatic heterocyclic group are linked. $R^1$, $R^2$, and $R^3$ are optionally bonded to any adjacent substituent to form a ring or form a fused ring with an adjacent ring.

The substituent is preferably an alkyl group having 1 to 10 carbon atoms, an alkenyl group having 1 to 10 carbon atoms, a substituted or unsubstituted aromatic hydrocarbon group having 6 to 20 carbon atoms, a substituted or unsubstituted aromatic heterocyclic group having 4 to 20 carbon atoms and containing a five-membered heterocyclic structure, or a substituted or unsubstituted linked aromatic group in which two to six of any one or more of the aromatic hydrocarbon group or the aromatic heterocyclic group are linked. The substituent is further preferably a substituted or unsubstituted aromatic hydrocarbon group having 6 to 18 carbon atoms, an aromatic heterocyclic group having 4 to 12 carbon atoms and containing a pyrrole ring, a furan ring, or a thiophene ring as the five-membered heterocyclic structure, or a substituted or unsubstituted linked aromatic group formed by linking of two to four of any one or more of the aromatic hydrocarbon group or the aromatic heterocyclic group.

The alkyl group of $R^1$, $R^2$, and $R^3$ having 1 to 20 carbon atoms may be any of linear, branched, and cyclic alkyl groups, and is preferably a linear, branched, or cyclic alkyl group having 1 to 10 carbon atoms. Specific examples thereof include: linear saturated hydrocarbon groups, such as a methyl group, an ethyl group, a n-propyl group, a n-butyl group, a n-pentyl group, a n-hexyl group, a n-octyl group, a n-dodecyl group, a n-tetradecyl group, and a n-octadecyl group; branched saturated hydrocarbon groups, such as an isopropyl group, an isobutyl group, a neopentyl group, a 2-ethylhexyl group, and a 2-hexyloctyl group; and saturated alicyclic hydrocarbon groups, such as a cyclopentyl group, a cyclohexyl group, a cyclooctyl group, a 4-butylcyclohexyl group, and a 4-dodecylcyclohexyl group.

Examples of the alkenyl group of $R^1$, $R^2$, and $R^3$ having 1 to 20 carbon atoms include a group in which hydrogens are eliminated from an alkyl group exemplified as the above alkyl group having 1 to 20 carbon atoms to convert a single bond into a double bond.

Of $R^1$, $R^2$, and $R^3$, examples of the aromatic hydrocarbon group having 6 to 30 carbon atoms or the aromatic heterocyclic group having 4 to 30 carbon atoms and containing the five-membered heterocyclic structure include the aromatic hydrocarbon group having 6 to 30 carbon atoms or the aromatic heterocyclic group having 4 to 30 carbon atoms and containing the five-membered heterocyclic structure described as the $Ar^3$. Preferable examples thereof include the same groups.

When the aromatic hydrocarbon group, the aromatic heterocyclic group containing the five-membered heterocyclic structure, or the linked aromatic group formed by linking of two to six of any one or more of the aromatic hydrocarbon group or the aromatic heterocyclic group have a substituent, examples of the substituent include an alkyl group having 1 to 20 carbon atoms. The alkyl group having 1 to 20 carbon atoms may be any of linear, branched, and cyclic alkyl groups, and is preferably a linear, branched, or cyclic alkyl group having 1 to 10 carbon atoms. Specific examples thereof include: linear saturated hydrocarbon groups, such as a methyl group, an ethyl group, a n-propyl group, a n-butyl group, a n-pentyl group, a n-hexyl group, a n-octyl group, a n-dodecyl group, a n-tetradecyl group, and a n-octadecyl group; branched saturated hydrocarbon groups, such as an isopropyl group, an isobutyl group, a neopentyl group, a 2-ethylhexyl group, and a 2-hexyloctyl group; and saturated alicyclic hydrocarbon groups, such as a cyclopentyl group, a cyclohexyl group, a cyclooctyl group, a 4-butylcyclohexyl group, and a 4-dodecylcyclohexyl group.

In the formula (2), "c", which represents the number of substitutions of $R^1$, represents an integer of 0 to 4. "d", which represents the number of substitutions of $R^2$, represents an integer of 0 to 2. "e", which represents the number of substitutions of $R^3$, represents an integer of 0 to 4. Preferably, all of "c", "d", and "e" are an integer of 0 to 2.

In the general formula (1), $Ar^2$ each independently represents a substituted or unsubstituted aromatic heterocyclic group having 3 to 30 carbon atoms and containing a nitrogen-containing six-membered cyclic structure, or a substituted or unsubstituted linked aromatic group which contains at least one of the aromatic heterocyclic group and in which two to seven of any one or more of the aromatic heterocyclic group or the hydrocarbon aromatic group having 6 to 30 carbon atoms are linked. Note that, a group bonded to L is the aromatic heterocyclic group.

$Ar^2$ is preferably: a substituted or unsubstituted aromatic heterocyclic group having 3 to 20 carbon atoms and containing a nitrogen-containing six-membered cyclic structure; or a substituted or unsubstituted linked aromatic group in which two to four of the aromatic heterocyclic group having 3 to 20 carbon atoms and containing at least one nitrogen-containing six-membered cyclic structure, and the aromatic hydrocarbon group having 6 to 20 carbon atoms are linked. Note that, a group bonded to L is the aromatic heterocyclic group.

Examples of the aromatic heterocyclic group of $Ar^2$ having 3 to 30 carbon atoms and containing the nitrogen-containing six-membered structure include a group in which one or more carbon atoms in the hydrocarbon aromatic group having 6 to 30 carbon atoms and having a six-membered hydrocarbon aromatic group as a partial structure are replaced with nitrogen atoms.

As the hydrocarbon aromatic group having 6 to 30 carbon atoms, known aromatic hydrocarbons can be used. Examples thereof include groups in which one or more carbon atoms in an aromatic hydrocarbon group are replaced with nitrogen atoms. Examples of such a group include: monocyclic aromatic hydrocarbon groups, such as benzene; bicyclic aromatic hydrocarbon groups, such as naphthalene; tricyclic aromatic hydrocarbon groups, such as indacene, biphenylene, phenalene, anthracene, and phenanthrene; tetracyclic aromatic hydrocarbon groups, such as fluoranthene, acephenanthrylene, aceanthrylene, triphenylene, pyrene, chrysene, tetraphene, tetracene, and pleiadene; and pentacyclic aromatic hydrocarbon groups, such as picene, perylene, pentaphene, pentacene, tetraphenylene, and naphthoanthracene.

A group in which one or more carbon atoms are replaced with nitrogen atoms can be preferably used. The aromatic hydrocarbon group is further preferably a group having one to four nitrogen atoms. Specific examples thereof include: monocyclic nitrogen-containing aromatic ring groups, such as pyridine, pyrazine, pyrimidine, pyridazine, and triazine; bicyclic nitrogen-containing aromatic ring groups, such as quinoline, isoquinoline, naphthyridine, phthalazine, quinoxaline, quinazoline, cinnoline, and pteridine; tricyclic nitrogen-containing aromatic ring groups, such as phenanthridine, acridine, phenanthroline, phenazine, anthyridine, and phenazone; and tetracyclic nitrogen-containing aromatic ring groups, such as thebenidine. Particularly preferable examples thereof include monocyclic nitrogen-containing aromatic ring groups, such as pyridine, pyrazine, pyrimidine, pyridazine, and triazine.

Here, the aromatic heterocyclic group of $Ar^2$ containing the nitrogen-containing six-membered cyclic structure may be a structure in which a nitrogen-containing six-membered cyclic structure such as a pyridine ring, a pyrazine ring, a pyrimidine ring, a pyridazine ring, and a triazine ring is singly present, or may be a structure in which such a nitrogen-containing six-membered cyclic structure is present fused with an aromatic ring such as a benzene ring.

$Ar^2$ also preferably contains at least one substituted or unsubstituted azine skeleton. In this case, the unsubstituted azine ring skeleton can be represented by an aromatic heterocyclic ring containing at least one N, as represented by the following formulae (3) to (7). Examples thereof include quinoline, quinoxaline, pyridine, pyrimidine, or triazine. $Ar^2$ preferably contains at least one pyridine, pyrimidine, or triazine skeleton, and more preferably contains at least one or more triazone skeletons. $Ar^2$ containing at least one substituted or unsubstituted azine skeleton is referred to, as a form where $Ar^2$ represents a substituted or unsubstituted aromatic heterocyclic group having 3 to 30 carbon atoms and containing the nitrogen-containing six-membered cyclic structure or a substituted or unsubstituted linked aromatic group which contains at least one of the aromatic heterocyclic group and in which two to seven of any one or more of the aromatic heterocyclic group or the aromatic hydrocarbon group having 6 to 30 carbon atoms are linked, a case where $Ar^2$ contains at least one substituted or non-substituted tricyclic fused skeleton.

[C 5]

(3)

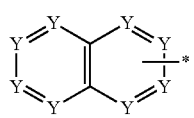
(4)

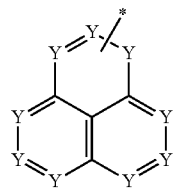
(5)

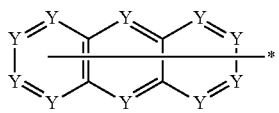
(6)

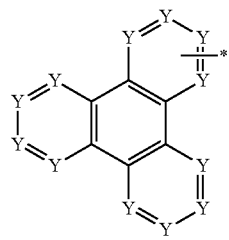
(7)

In the formulae (3) to (7), "*" represents a bonding position to L in the formula (1), Y represents N, CH or C—, and at least one Y represents N. Here, C— represents a case where Y is linked with another aromatic heterocyclic group or aromatic hydrocarbon group. Note that, the formulae (3) to (7) may have a substituent, and the substituent in this case is the same as the substituent that $Ar^2$ can have.

When $Ar^2$ is the aromatic heterocyclic group having 3 to 30 carbon atoms and containing at least one nitrogen-containing six-membered cyclic structure and when $Ar^2$ is the linked aromatic group in which two to seven aromatic hydrocarbon groups having 6 to 30 carbon atoms are linked, examples of the hydrocarbon aromatic group having 6 to 30 carbon atoms include the aromatic hydrocarbon group having 6 to 30 carbon atoms described in the $Ar^3$.

Examples of the substituent that $Ar^2$ can have include an alkyl group having 1 to 20 carbon atoms, which is the same as the aforementioned alkyl group having 1 to 20 carbon atoms.

In the general formula (1), "a" represents the number of substitutions, and represents an integer of 1 to 6. "a" is preferably an integer of 1 to 4, more preferably 1 to 3, and further preferably 1 to 2.

Preferable specific examples of the material for a photoelectric conversion element for imaging of the present invention represented by the general formula (1) are shown below, but the material is not limited thereto.

[C 6]

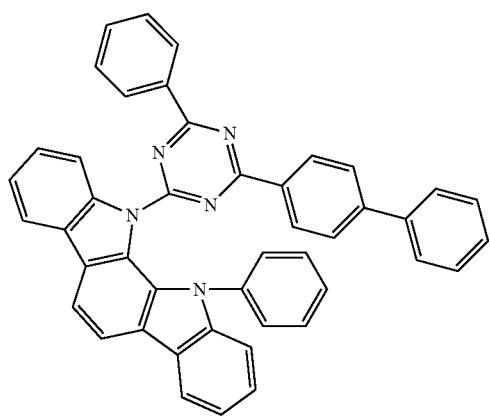
(W1)

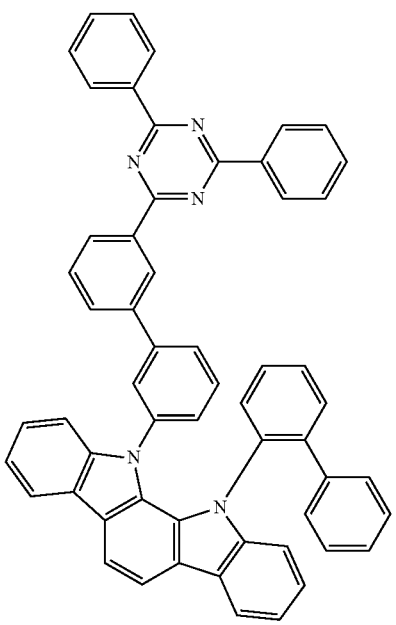
(W2)

-continued
(W3)
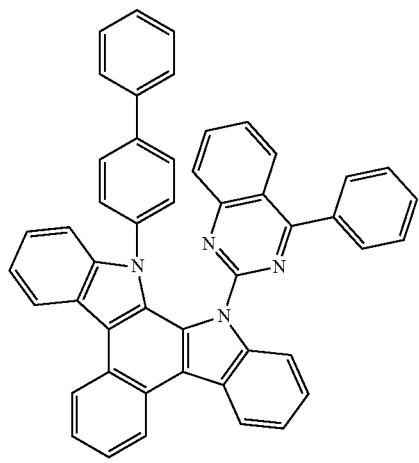
(W4)
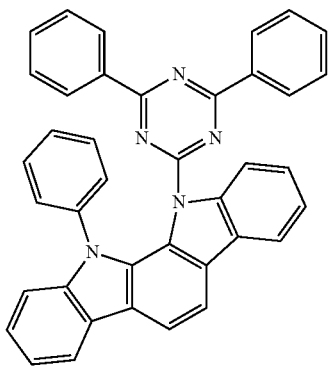
(W5)
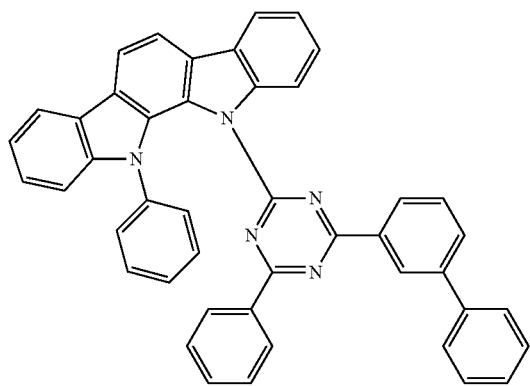
(W6)
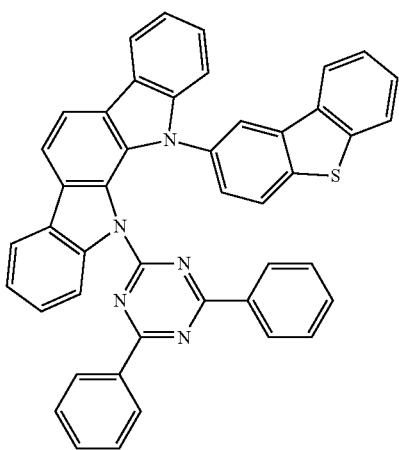
(W7)
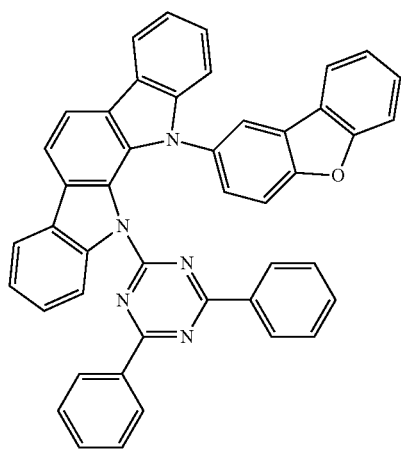
(W8)
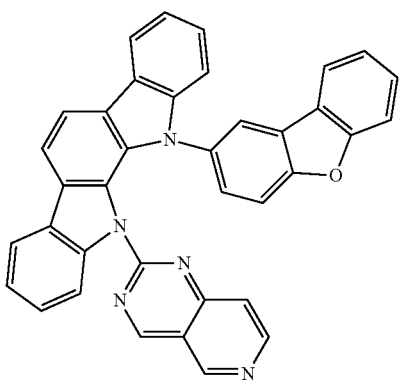

[C 7]
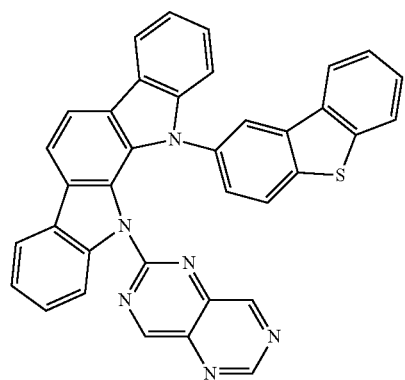
-continued
(W9)
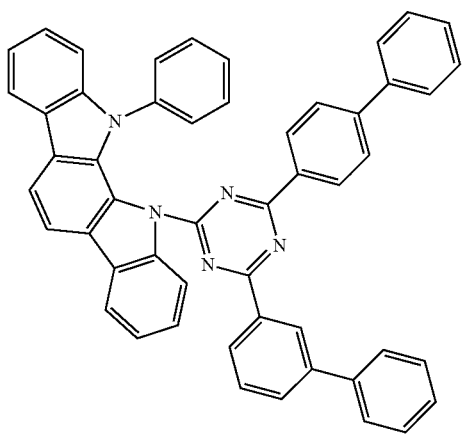
(W10)
(W11)
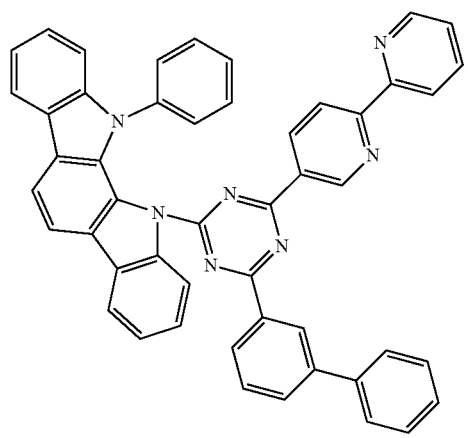
(W12)
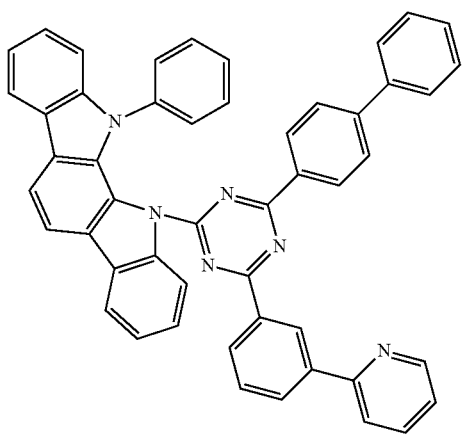
(W13)
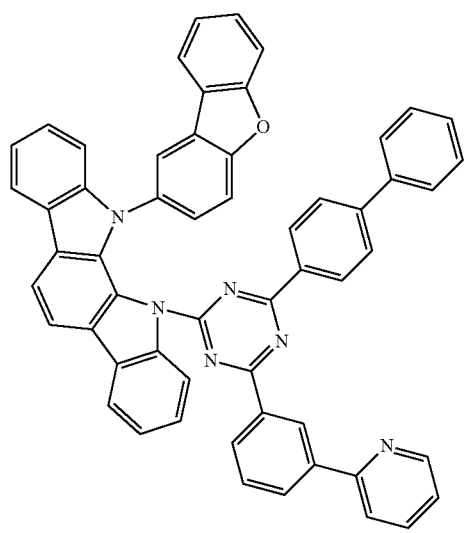
(W14)
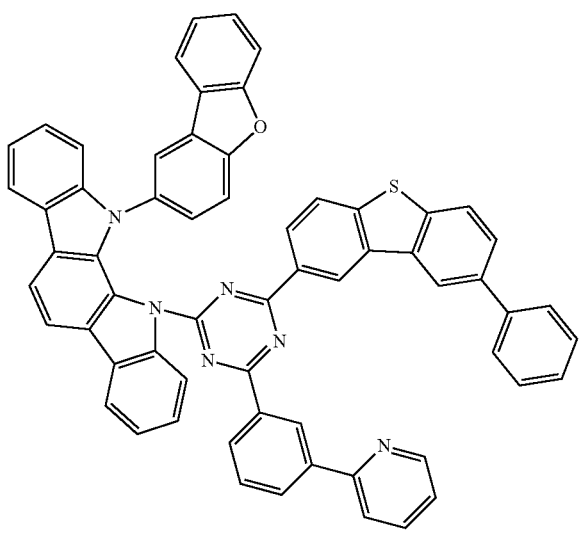

-continued
(W15)
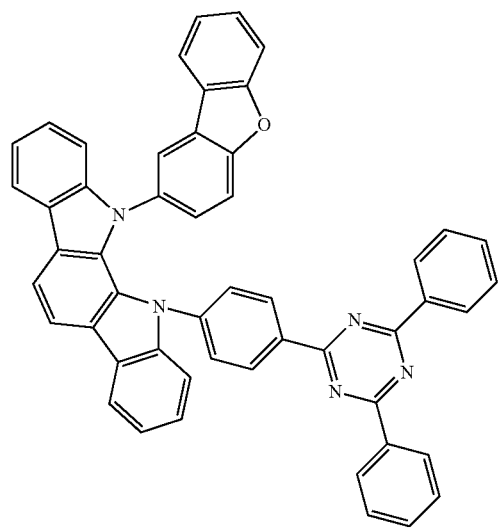
(W16)
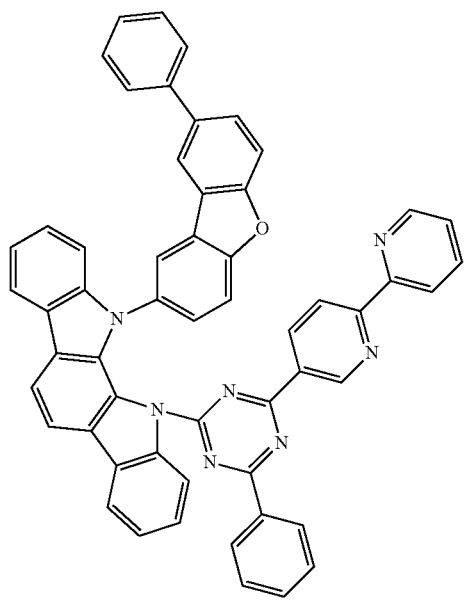
[C 8]
(W17)
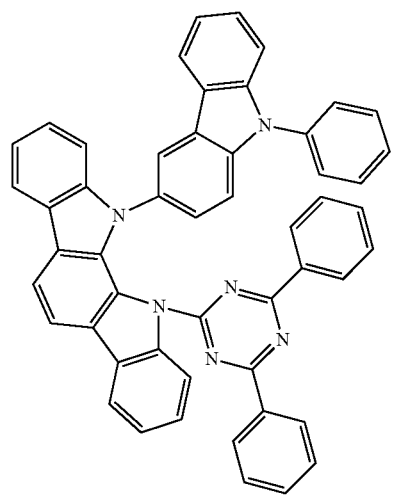
(W18)
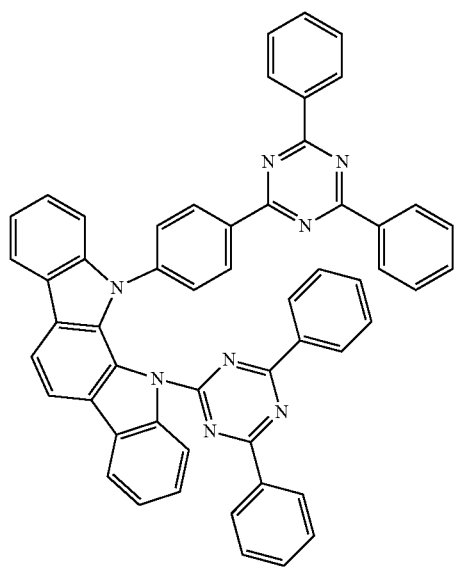

-continued
(W19)
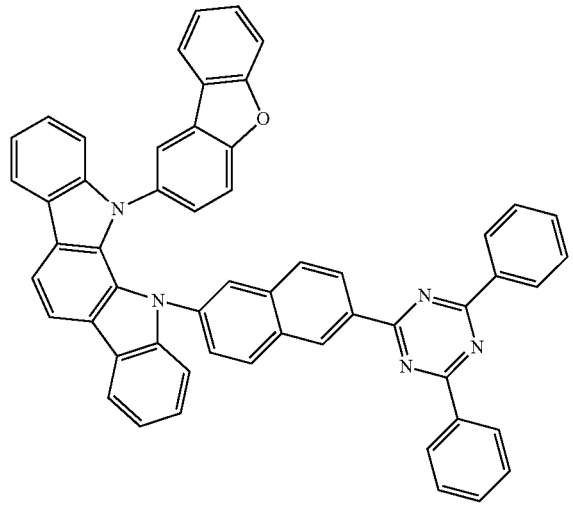
(W20)
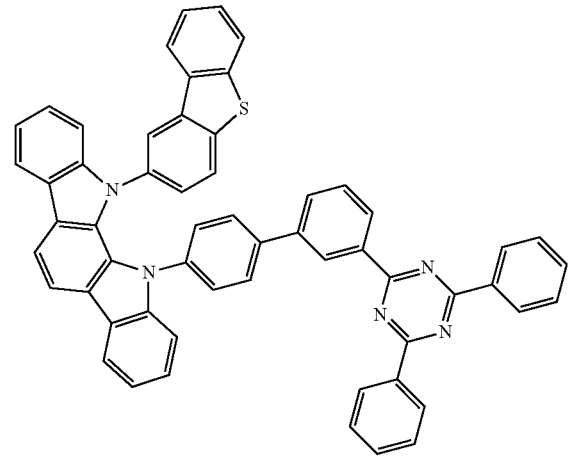
(W21)
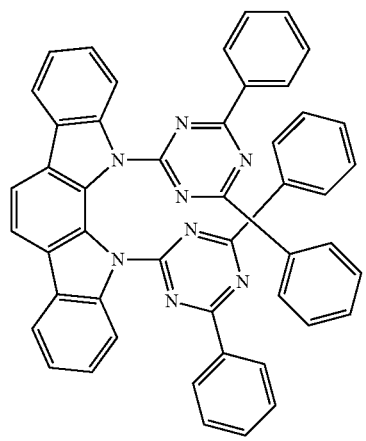
(W22)
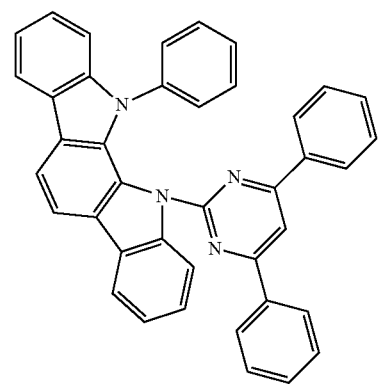
(W23)
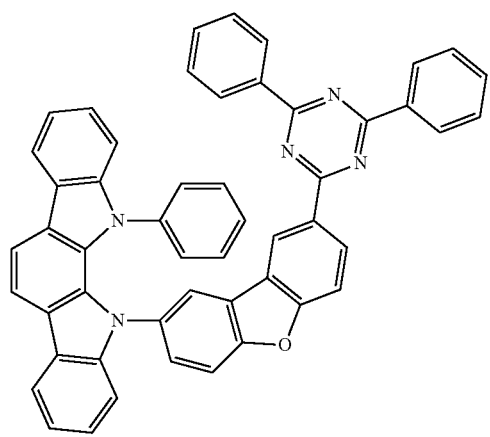
(W24)
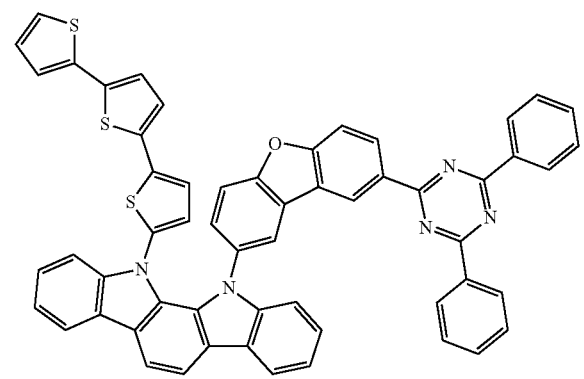

-continued
[C 9]
(W25)
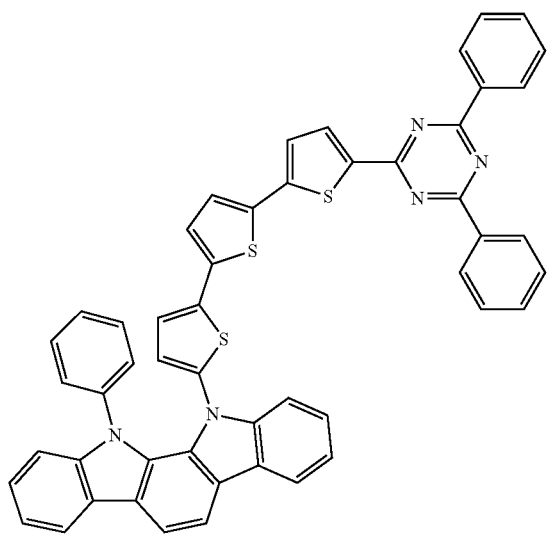
(W26)
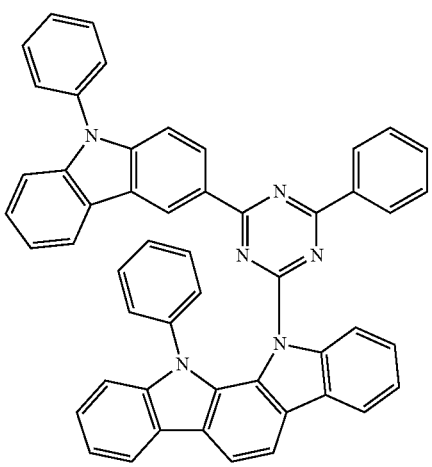
(W27)
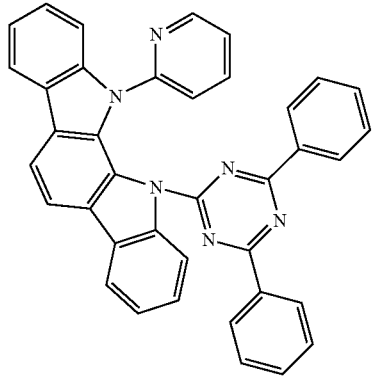
(W28)
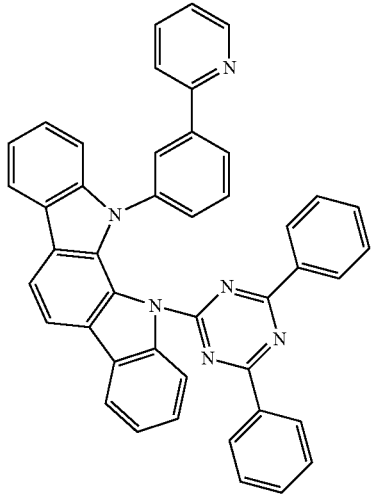
(W29)
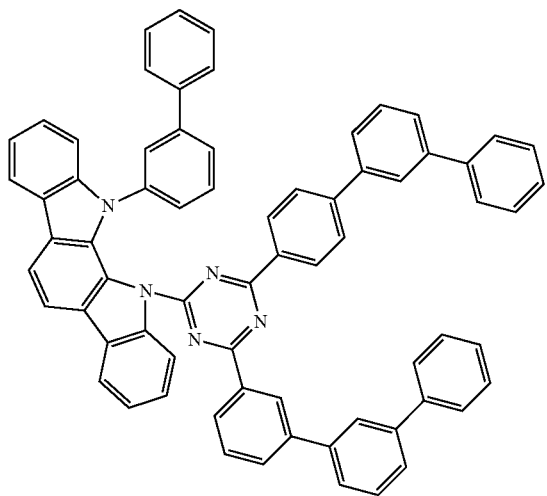
(Wd1)
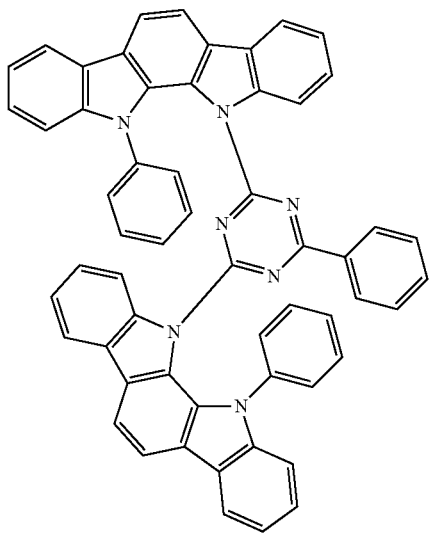

(Wd2)
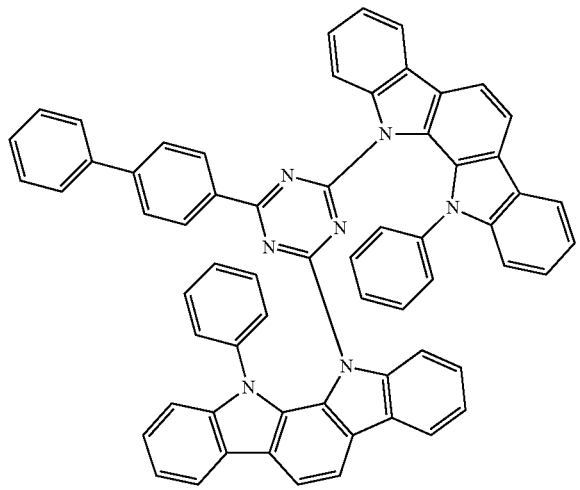
[C 10]
(Wd3)
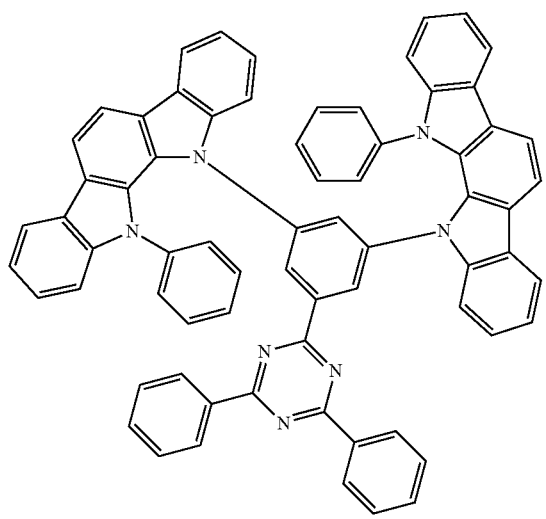
(Wd4)
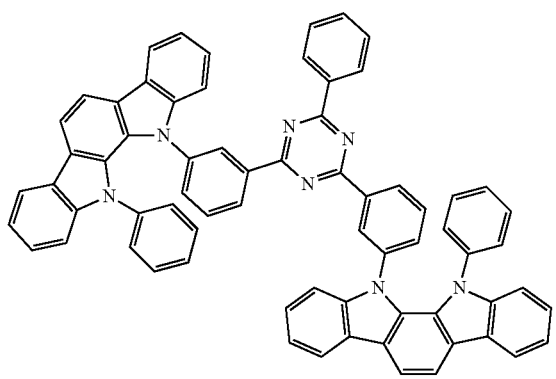
(Wd5)
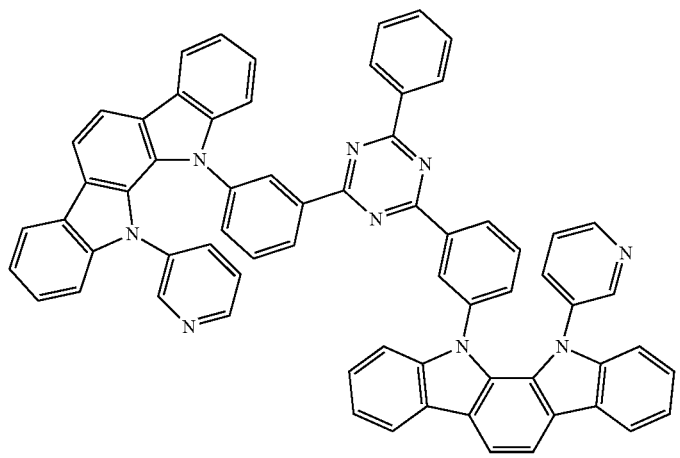

(Wd6)
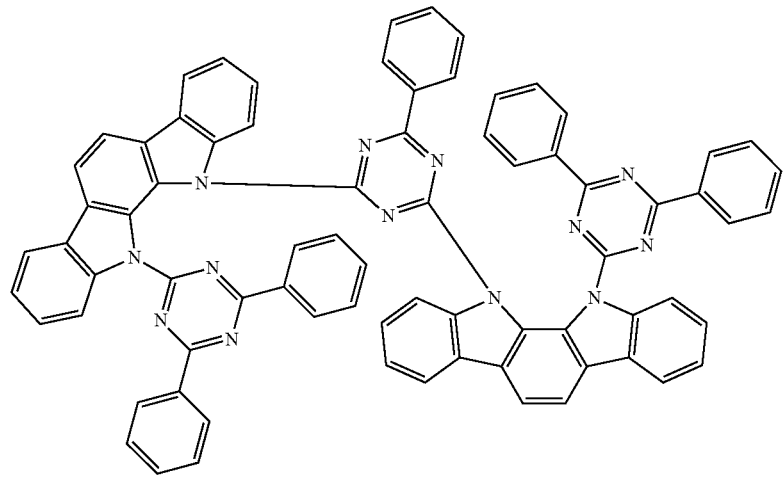
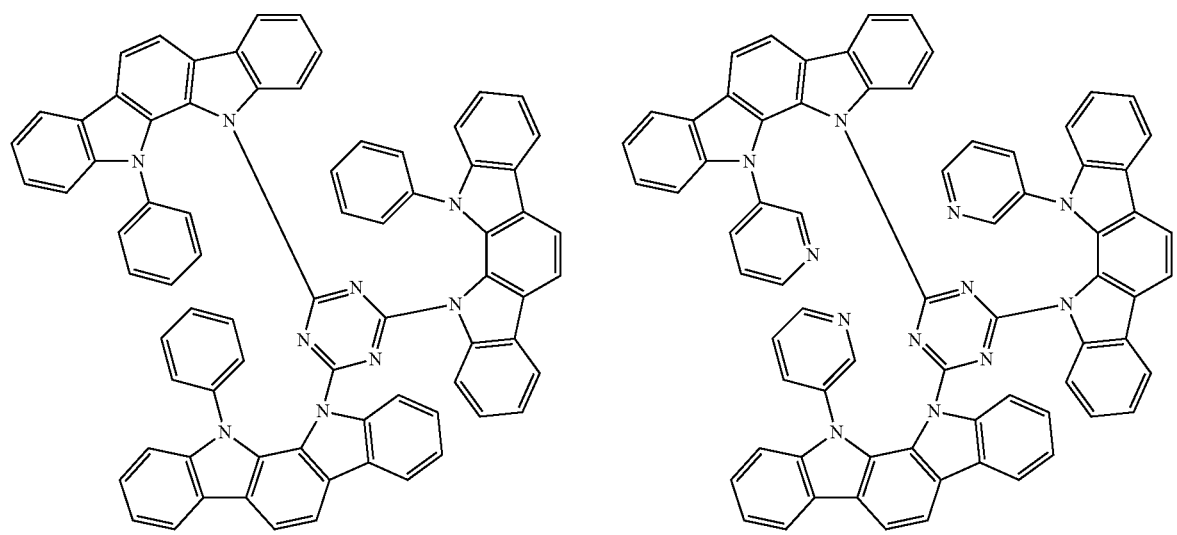
(Wd7) (Wd8)
[C 11]
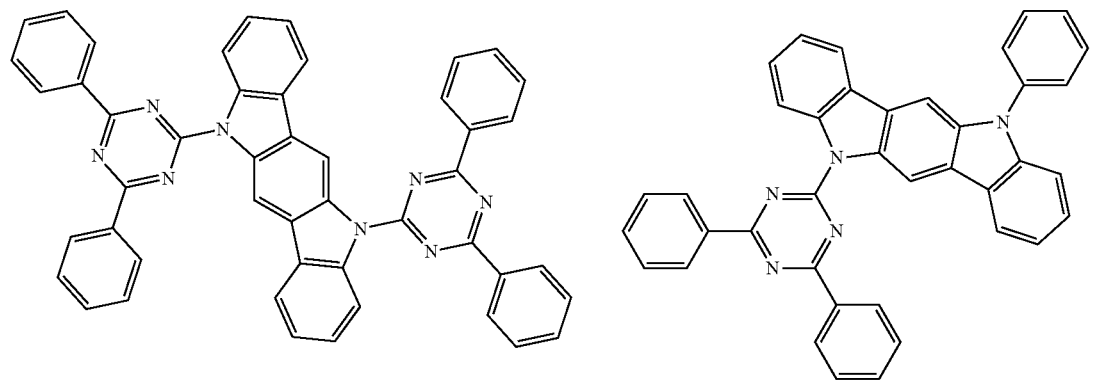
(Y1) (Y2)

-continued
(Y3)
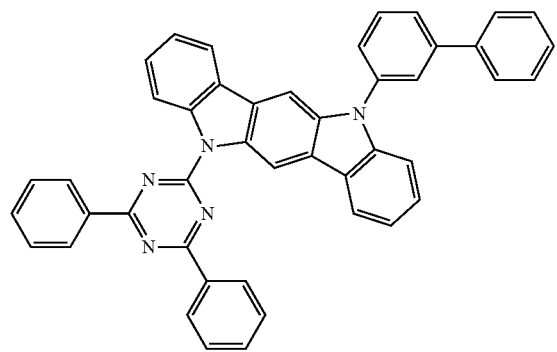
(Y4)
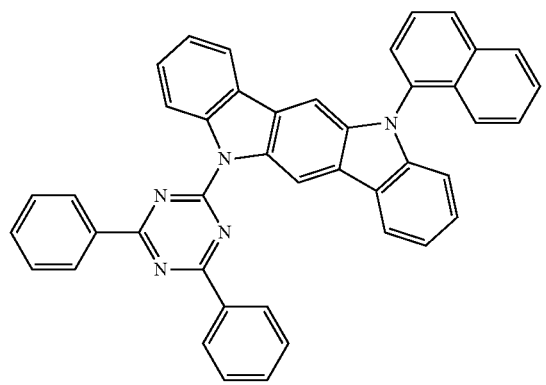
(Y5)
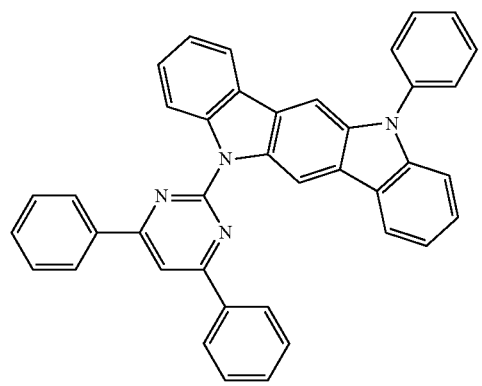
(Y6)
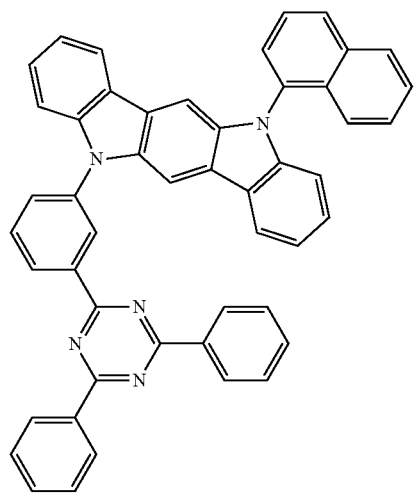
(Y7)
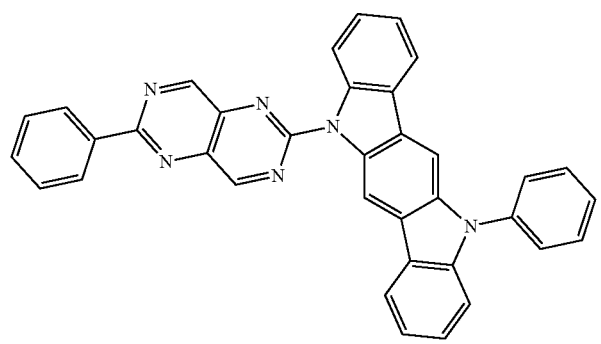
(Y8)
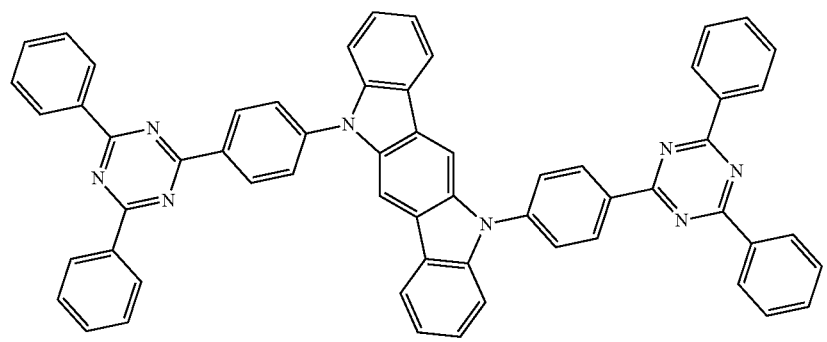

-continued
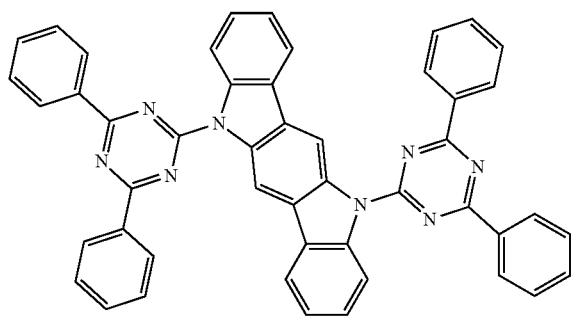
(Y9)
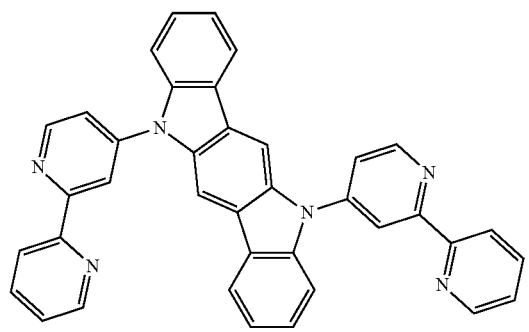
(Y10)
[C 12]
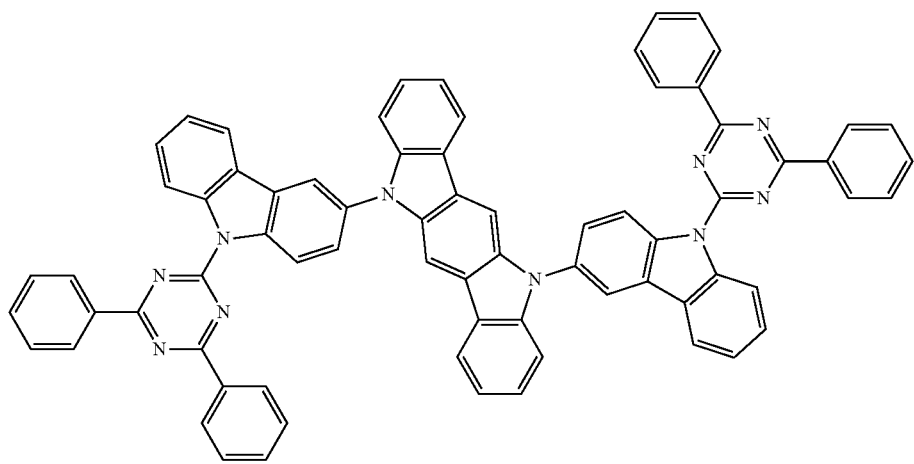
(Y11)
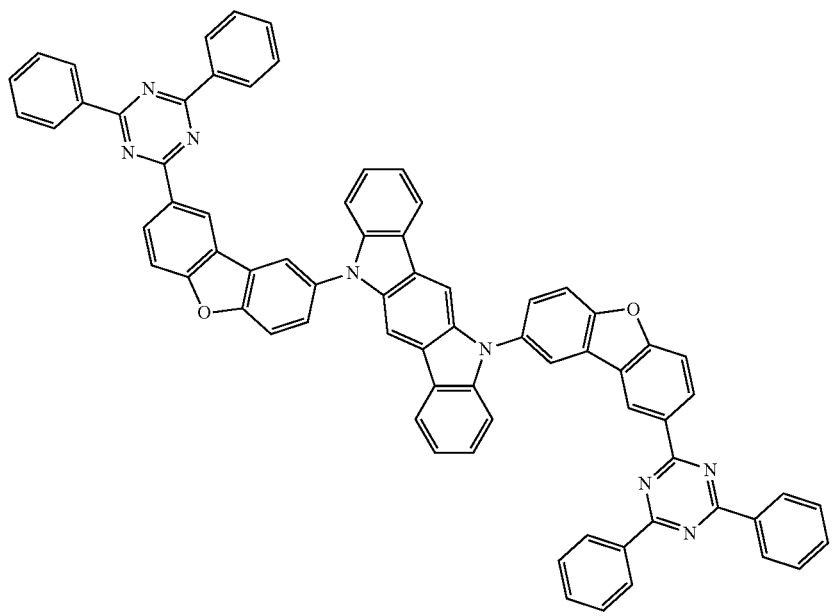
(Y12)

-continued
(U1)
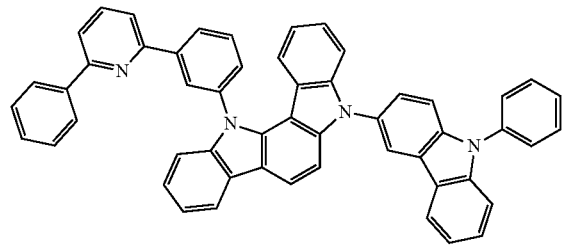
(U2)
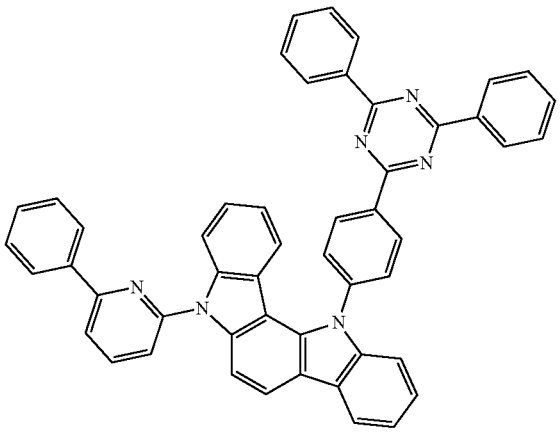
[C 13]
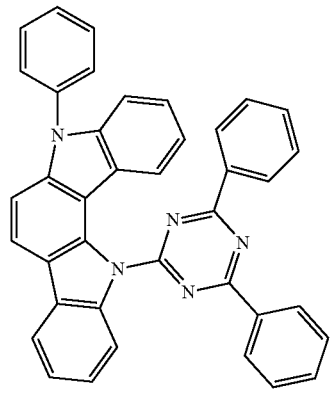
(U3)
(U4)
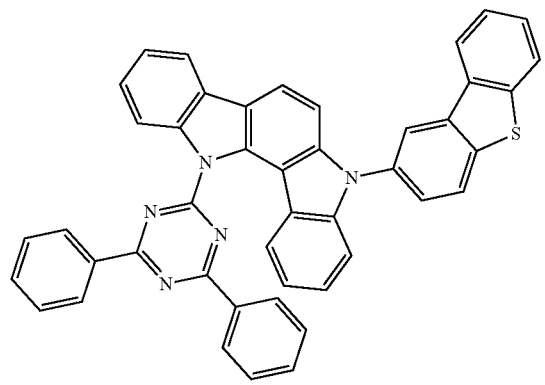
(U5)
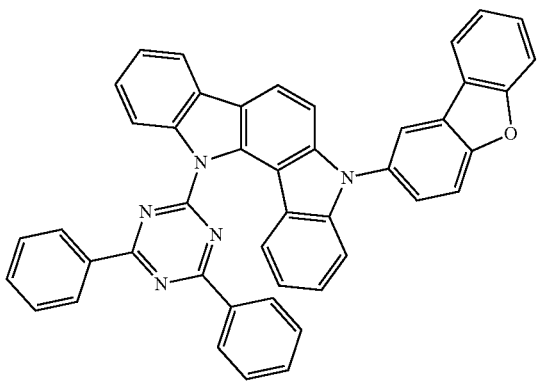
(U6)
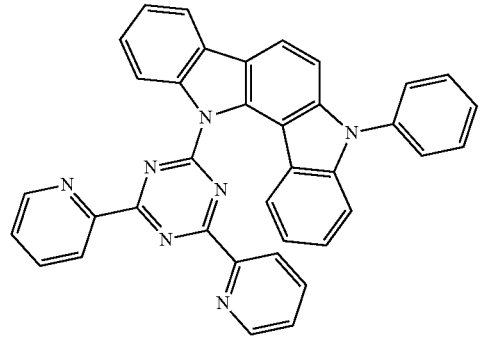
(U7)
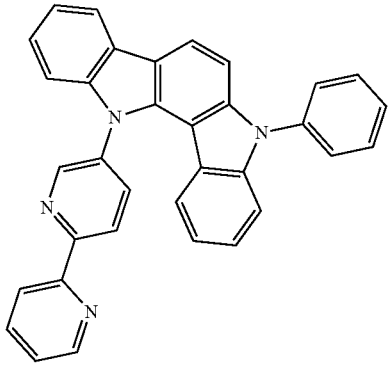

(U8)
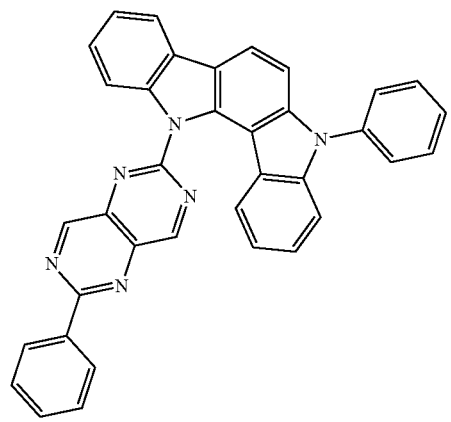
(U9)
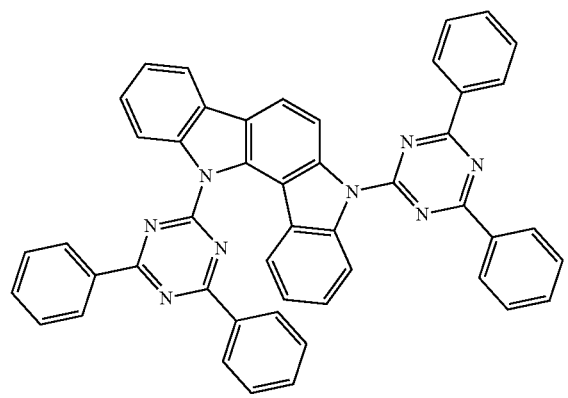
(U10)
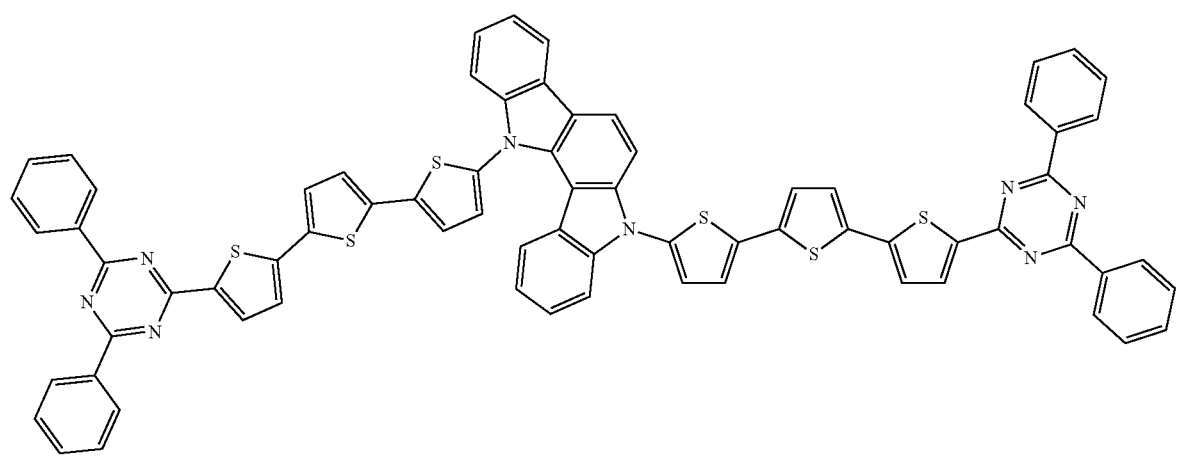
(U11)
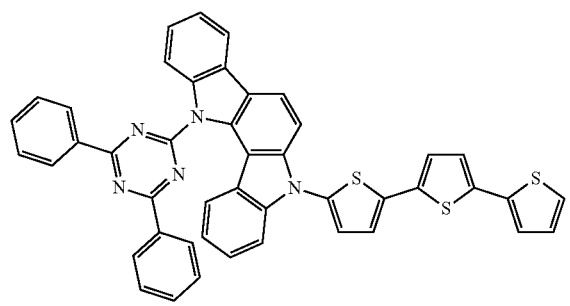
(U12)
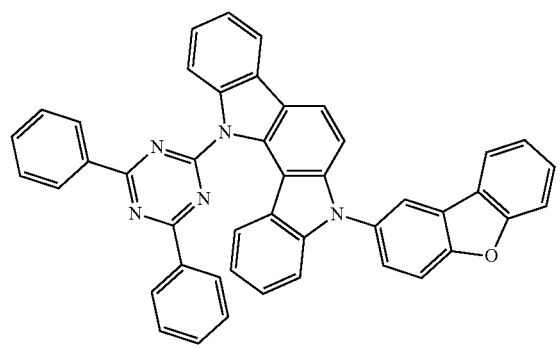

[C 14]
-continued
(U13)
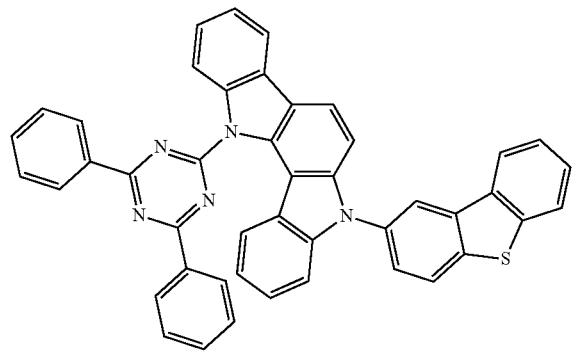
(U14)
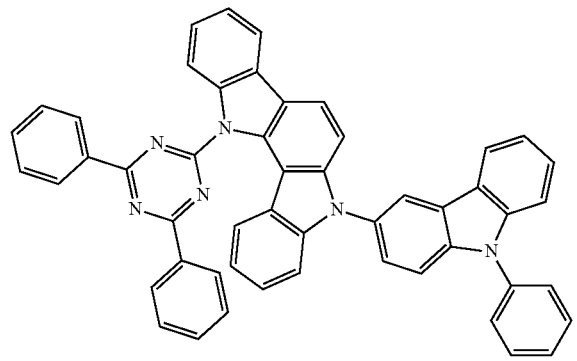
(U15)
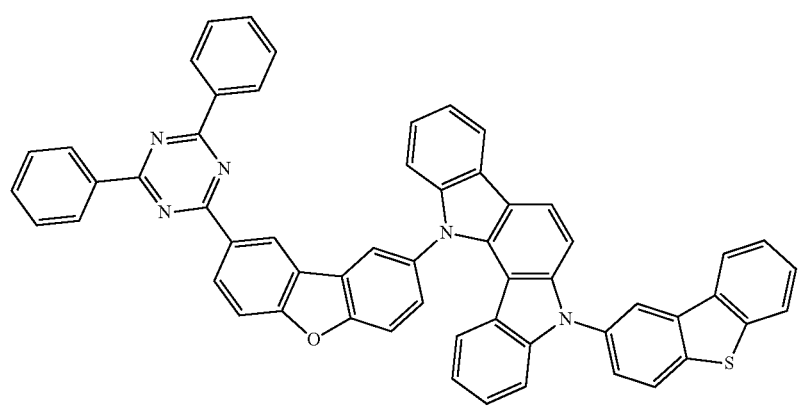
(U16)
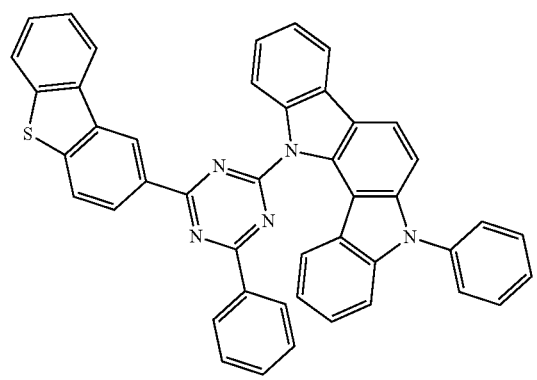
(U17)
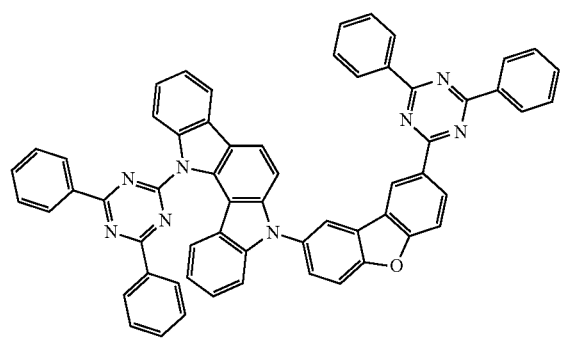
(U18)
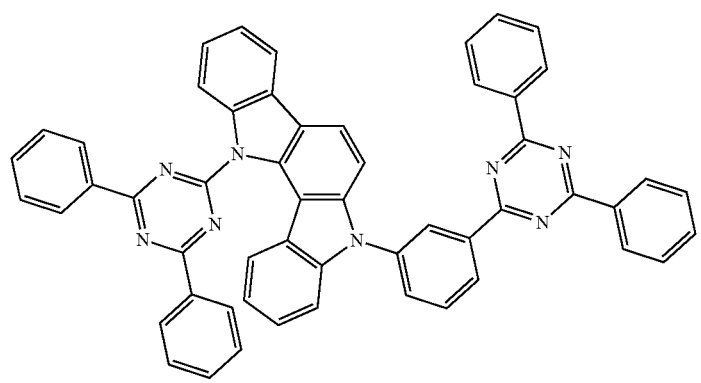

[C 15]
(U19)
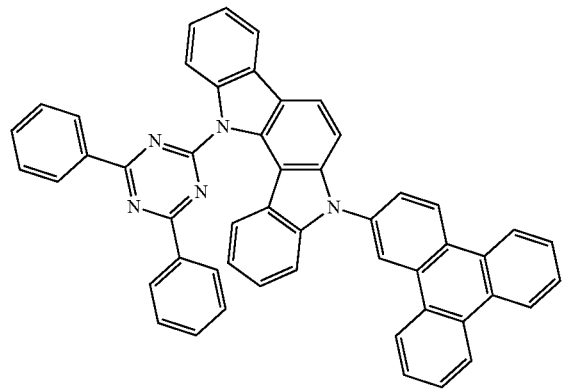
(U20)
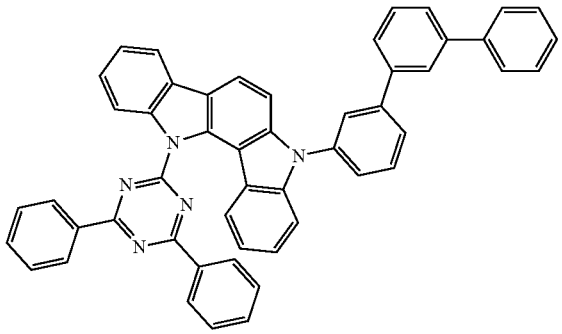
(U21)
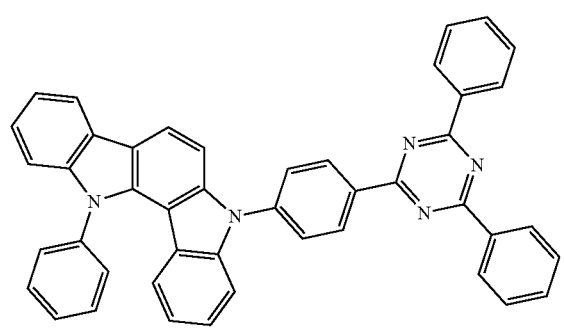
(Vd1)
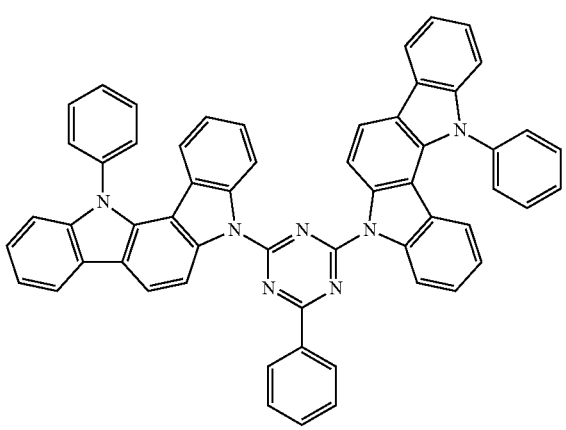
(Vd2)
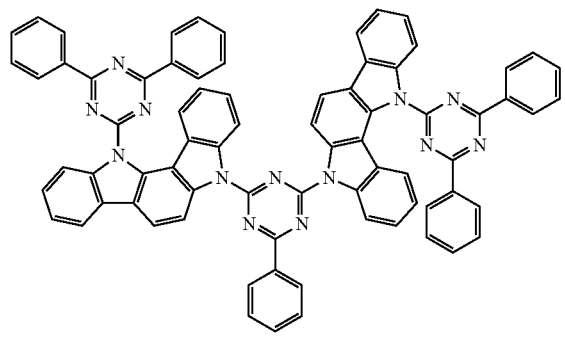
(Ud1)
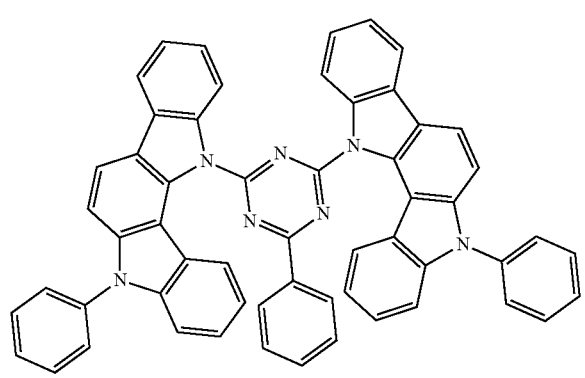

[C 16]
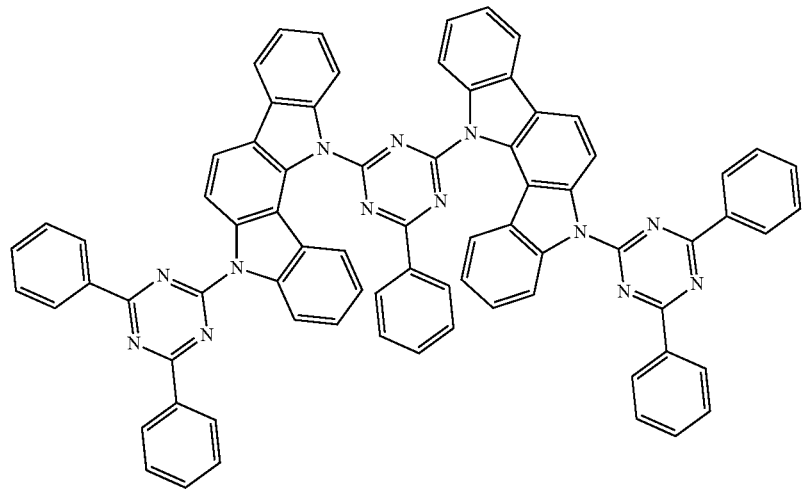
(Ud2)
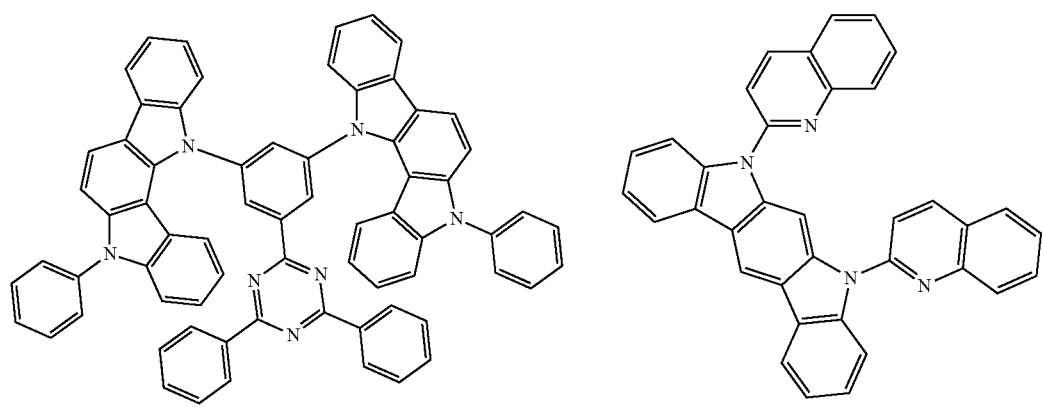
(Ud3)
(Z1)
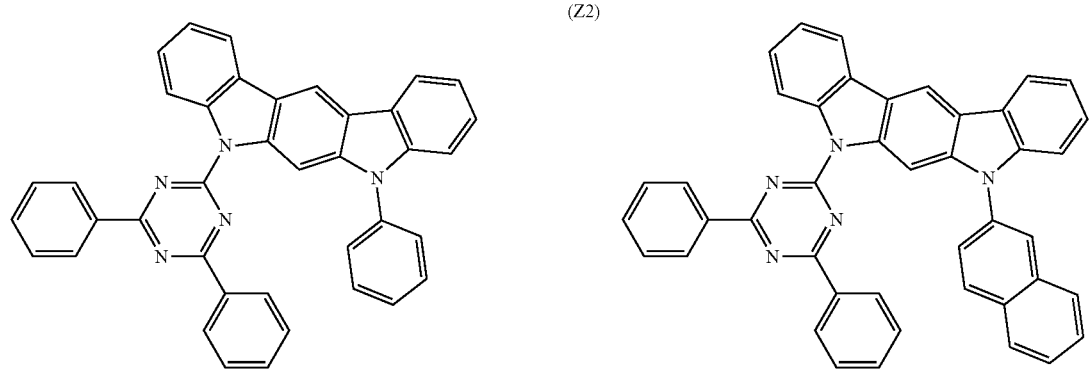
(Z2)
(Z3)

(Z4)
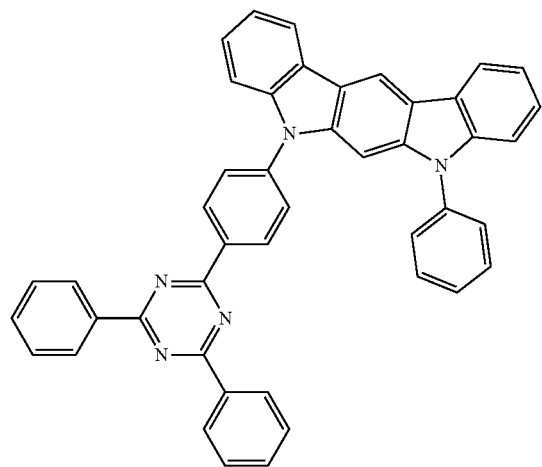
[C 17]
(X1)
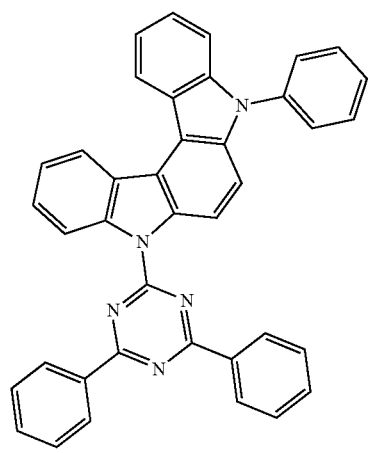
(X2)
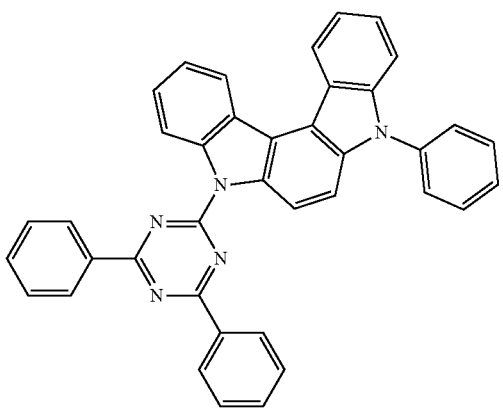
(X4)
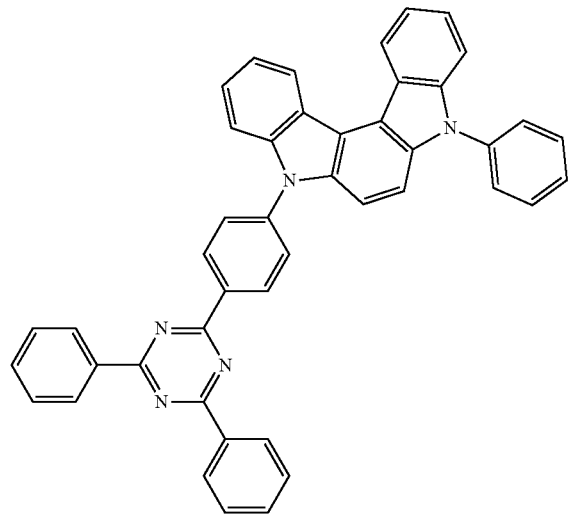
(G1)
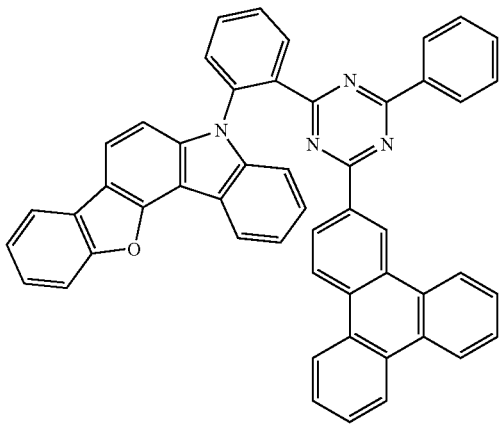

-continued
(G2)
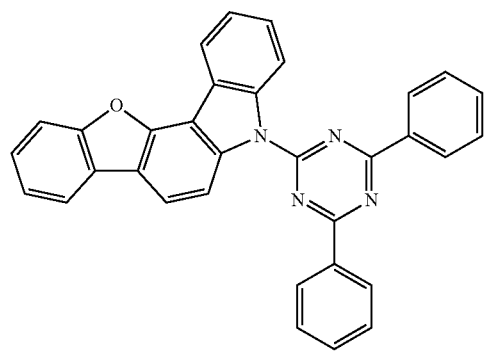
(G3)
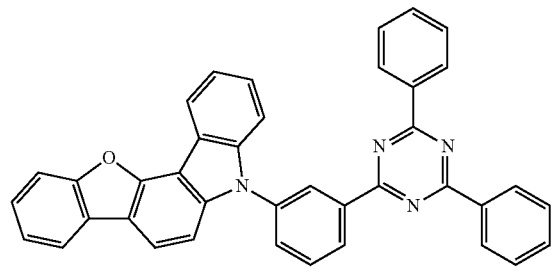
(G4)
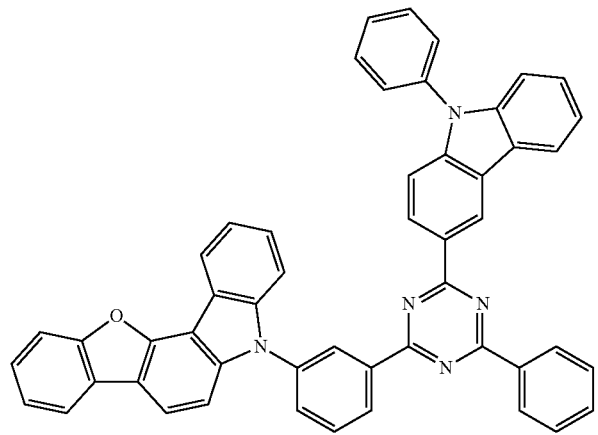
[C 18]
(G5)
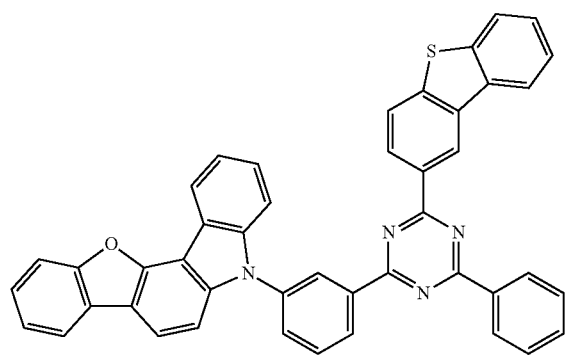
(G6)
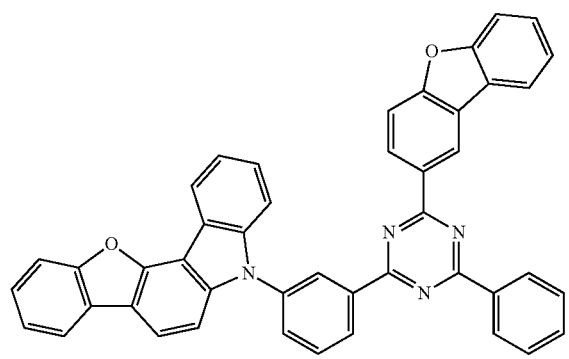

(G7)
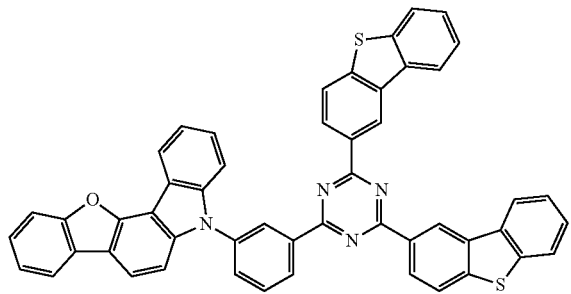
(Gd2)
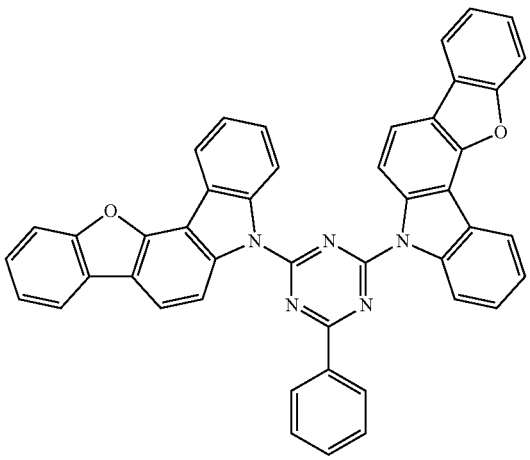
(Gd3)
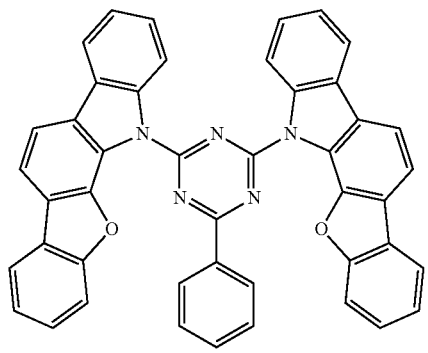
(Gd4)
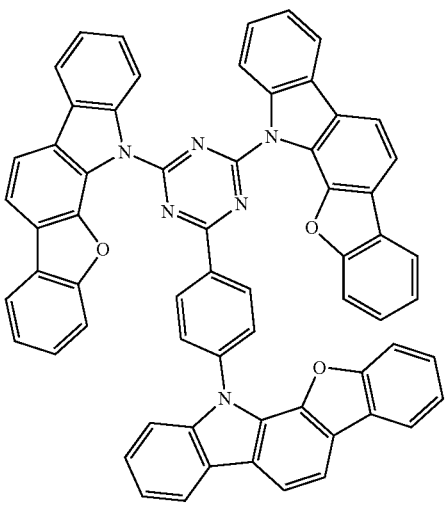
[C 19]
(Gd5)
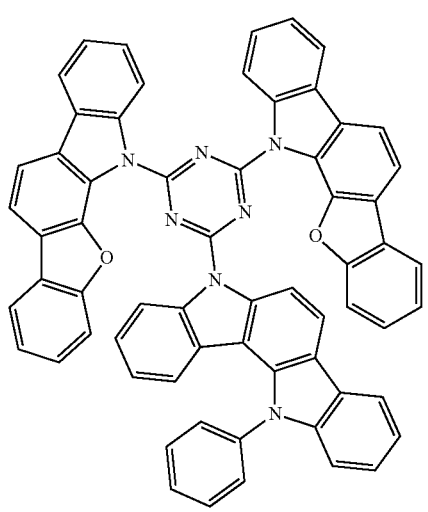
(H1)
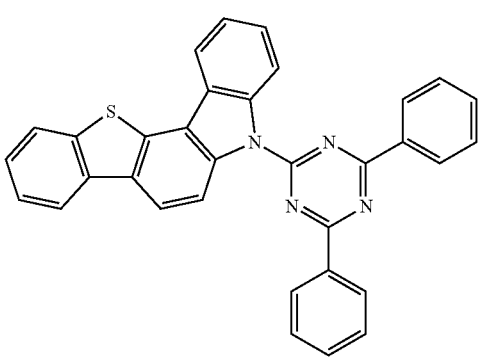

-continued
(H2)
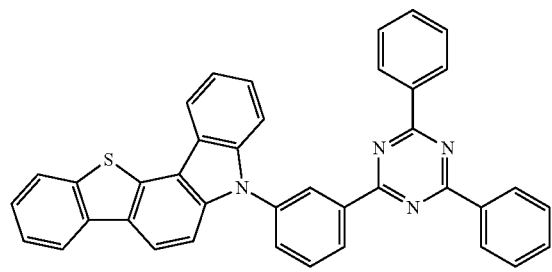
(H3)
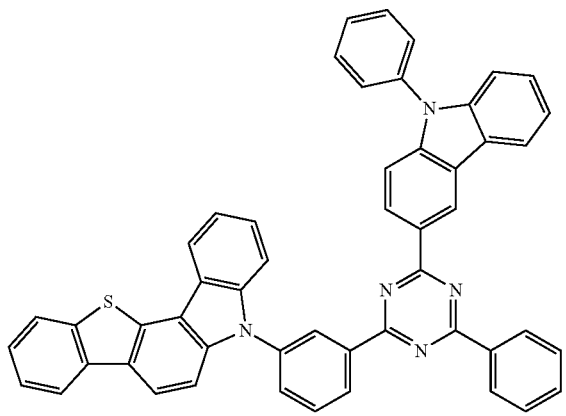
(H4)
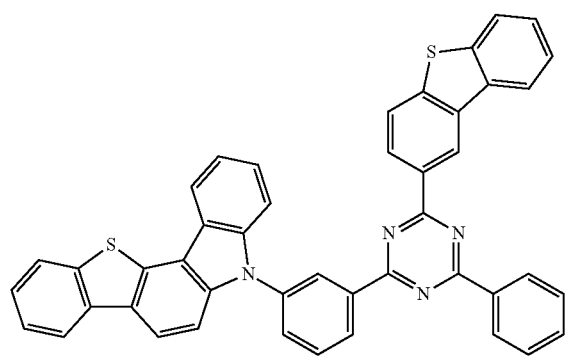
(H5)
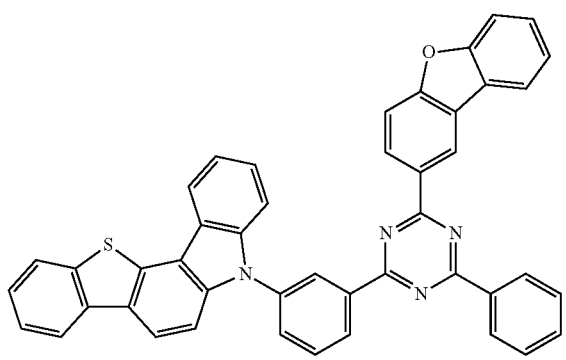
(H6)
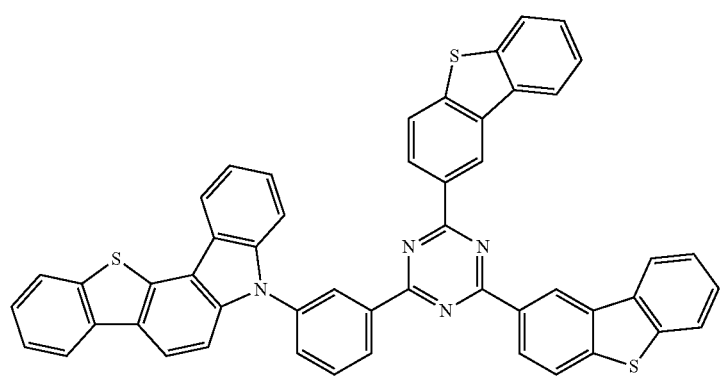

[C 20]
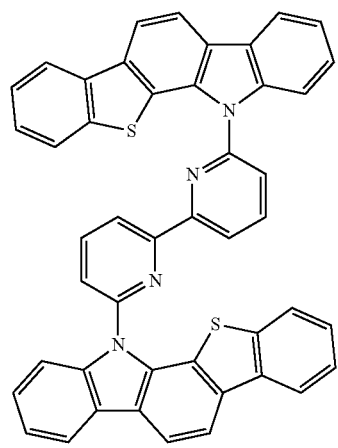
(Hd1)
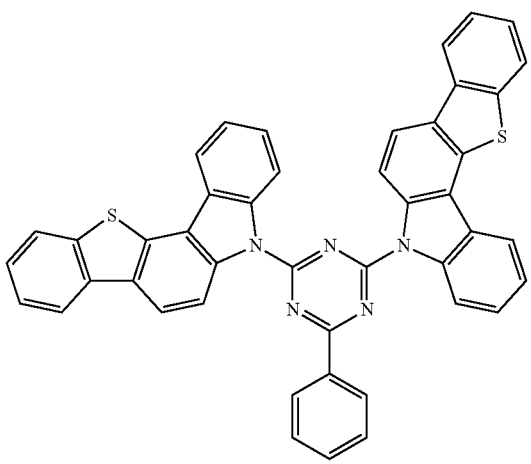
(Hd2)
(Hd3)
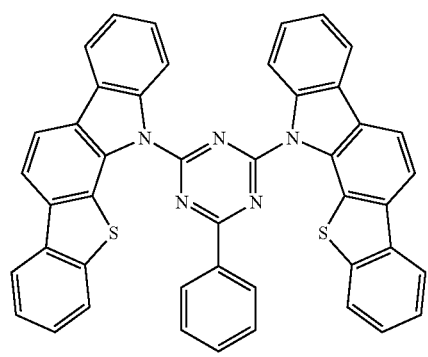
(Hd4)
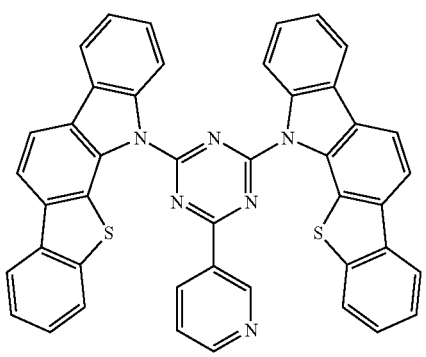
(Hd5)
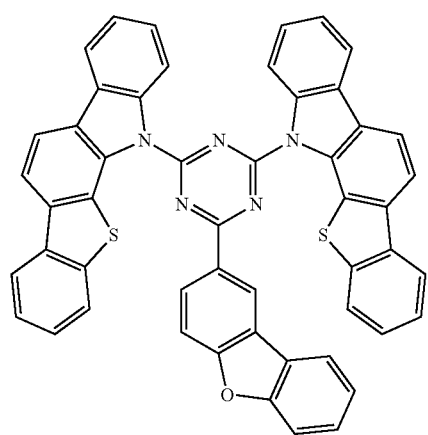
(Hd6)
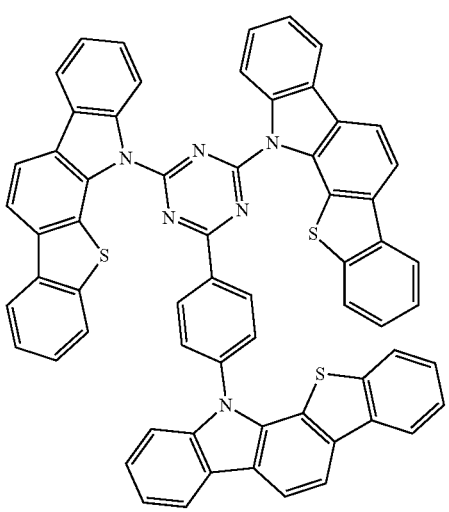

-continued
(Jd1)
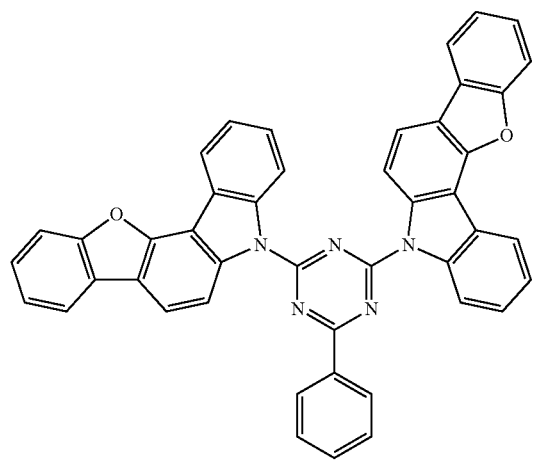
(Jd2)
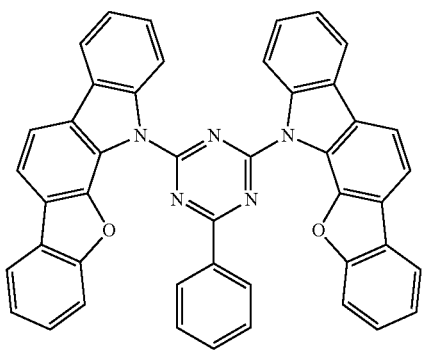
[C 21]
(Jd3)
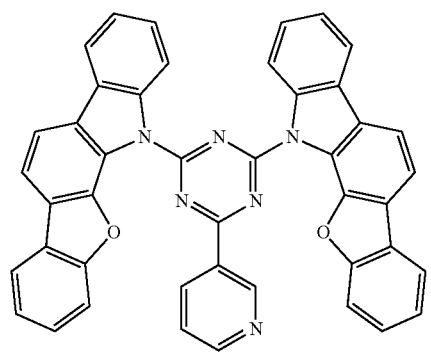
(Jd4)
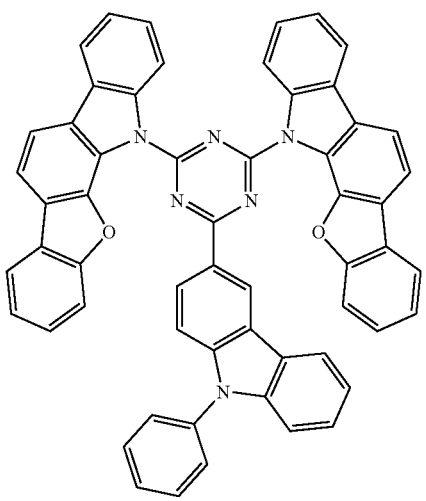
(Jd5)
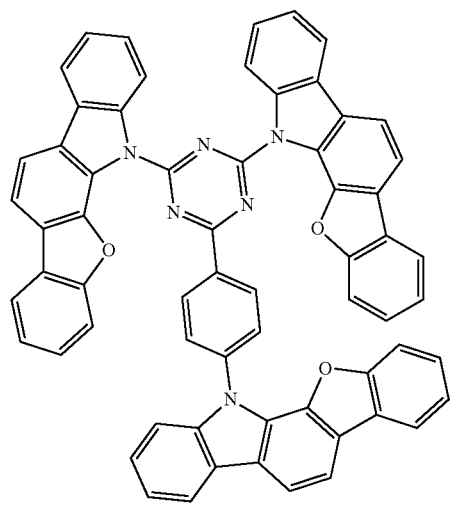

The material for the photoelectric conversion element for imaging of the present invention represented by the general formula (1) can be obtained by: synthesis by methods of various organic synthetic reactions established in the field of the organic synthetic chemistry including coupling reactions such as Suzuki coupling, Stille coupling, Grignard coupling, Ullmann coupling, Buchwald-Hartwig reaction, and Heck reaction, using commercially available reagents as raw materials; and then purification by using a known method such as recrystallization, column chromatography, and sublimation and purification. The method is not limited to this method.

The material for a photoelectric conversion element for imaging of the present invention preferably has an energy level of highest occupied molecular orbital (HOMO) obtained by structural optimization calculation with a density functional calculation B3LYP/6-31G(d) of −4.5 eV or lower, more preferably within a range of −4.5 eV to −6.0 eV.

The material for a photoelectric conversion element for imaging of the present invention preferably has an energy level of lowest unoccupied molecular orbital (LUMO) obtained by structural optimization calculation with a density functional calculation B3LYP/6-31G(d) of −2.5 eV or higher, more preferably within a range of −2.5 eV to −0.5 eV.

In the material for a photoelectric conversion element for imaging of the present invention, a difference (absolute value) between the HOMO energy level and the LUMO energy level is preferably within a range of 2.0 to 5.0 eV, and more preferably within a range of 2.5 to 4.0 eV.

The material for a photoelectric conversion element for imaging of the present invention preferably has a hole mobility of $1\times10^{-6}$ cm$^2$/Vs to 1 cm$^2$/Vs, more preferably has a hole mobility of $1\times10^{-5}$ cm$^2$/Vs to $1\times10^{-1}$ cm$^2$/Vs. The hole mobility can be evaluated by known methods such as a method with a FET-type transistor element, a method with a time-of-flight method, and an SCLC method.

The material for a photoelectric conversion element for imaging of the present invention is preferably amorphous. The amorphousness can be confirmed by various methods, and can be confirmed by, for example, detecting no peak in an XRD method or by detecting no endothermic peak in a DSC method.

Next, a photoelectric conversion element for imaging using the material for a photoelectric conversion element for imaging of the present invention will be described, but a structure of the photoelectric conversion element for imaging of the present invention is not limited thereto. The description will be made with reference to Drawing.

FIG. 1 is a sectional view schematically illustrating a structural example of the photoelectric conversion element for imaging using the material for a photoelectric conversion element for imaging of the present invention. In FIG. 1, 1 represents an electrode, 2 represents a hole blocking layer, 3 represents a photoelectric conversion layer, 4 represents an electron blocking layer, 5 represents an electrode, and 6 represents a substrate. The photoelectric conversion element is not limited to the element in FIG. 1, and adding or omitting a layer can be made as necessary.

Hereinafter, each member and each layer of the photoelectric conversion element of the present invention will be described.

Substrate

The photoelectric conversion element using the material for a photoelectric conversion element of the present invention is preferably supported on a substrate. The substrate is not particularly limited, and substrates made of glass, transparent plastic, quartz, and the like can be used, for example.

Electrode

An electrode used for the photoelectric conversion element for imaging using the material for a photoelectric conversion element for imaging of the present invention has a function of trapping a hole and an electrode generated in the photoelectric conversion layer. A function to let light enter the photoelectric conversion layer is also required. Thus, at least one of two electrodes is desirably transparent or semi-transparent. A material used for the electrode is not particularly limited as long as it has conductivity, and examples thereof include: conductive transparent materials, such as ITO, IZO, SnO2, ATO (antimony-doped tin oxide), ZnO, AZO (Al-doped zinc oxide), GZO (gallium-doped zinc oxide), TiO2, and FTO; metals, such as gold, silver, platinum, chromium, aluminum, iron, cobalt, nickel, and tungsten; inorganic conductive substances, such as copper iodide and copper sulfide; and conductive polymers, such as polythiophene, polypyrrole, and polyaniline. A plurality of these materials may be mixed to use as necessary. In addition, two or more layers thereof may be stacked.

Photoelectric Conversion Layer

The photoelectric conversion layer is a layer in which a hole and an electrode are generated by charge separation of an exciter generated by the incident light. The photoelectric conversion layer may be formed with a single photoelectric converting material, or may be formed by combination with a P-type organic semiconductor material being a hole transport material and an N-type organic semiconductor material being an electron transport material. Two or more kinds of the P-type organic semiconductor may be used, and two or more kinds of the N-type organic semiconductor may be used. One or more kinds of these P-type organic semiconductor and/or N-type organic semiconductor desirably use a dye material having a function of absorbing light with a desired wavelength in the visible region. As the P-type organic semiconductor material being the hole transport material, the compound of the present invention represented by the formula (1) can be used.

The P-type organic semiconductor material may be any material having a hole transportability. The material represented by the formula (1) is preferably used, but another P-type organic semiconductor material may be used. In addition, two or more kinds of the material represented by the formula (1) may be mixed to use. Furthermore, the formula (1) and another P-type organic semiconductor material may be mixed to use. The another P-type organic semiconductor material may be any material having the hole transportability, and for example, usable are: compounds having a fused polycyclic aromatic group such as naphthalene, anthracene, phenanthrene, pyrene, chrysene, naphthacene, triphenylene, perylene, fluoranthene, fluorene, and indene; compounds having a π-excess aromatic group such as a cyclopentadiene derivative, a furan derivative, a thiophene derivative, a pyrrole derivative, a benzofuran derivative, a dibenzothiophene derivative, a dinaphthothienothiophene derivative, an indole derivative, a pyrazoline derivative, a dibenzofuran derivative, a dibenzothiophene derivative, a carbazole derivative, and indolocarbazole derivative; an aromatic amine derivative, a styrylamine derivative, a benzidine derivative, a porphyrin derivative, a phthalocyanine derivative, and a quinacridone derivative.

In addition, examples of a polymer P-type organic semiconductor material include a polyphenylene-vinylene derivative, a polyparaphenylene derivative, a polyfluorene derivative, a polyvinylcarbazole derivative, and a polythiophene derivative. Two or more kinds selected from the compound of the present invention represented by the formula (1), the P-type organic semiconductor material, and the polymer P-type organic semiconductor material may be mixed to use.

The N-type organic semiconductor material may be any material having the electron transportability, and examples thereof include naphthalenetetracarboxylic diimide and perylenetetracarboxylic diimide, fullerenes, and azole derivatives such as imidazole, thiazole, thiadiazole, oxazole, oxadiazole, and triazole. Two or more kinds selected from the N-type organic semiconductor materials may be mixed to use.

Electron Blocking Layer

The electron blocking layer is provided in order to inhibit a dark current generated by injecting an electron from one electrode into the photoelectric conversion layer when a bias voltage is applied between the two electrodes. The electron blocking layer also has a function of hole transportation for transporting a hole generated by charge separation in the photoelectric conversion layer toward the electrode. A single layer or multiple layers of the electron blocking layer can be disposed as necessary. For the electron blocking layer, a P-type organic semiconductor material being the hole transport material can be used. The P-type organic semiconductor material may be any material having the hole transportability. Although the material represented by the formula (1) is preferably used, another P-type organic semiconductor material may be used. The material represented by the formula (1) and another P-type organic semiconductor material may be mixed to use. The other P-type organic semiconductor material may be any material having the hole transportability, and for example, usable are: compounds having a fused polycyclic aromatic group such as naphthalene, anthracene, phenanthrene, pyrene, chrysene, naphthacene, triphenylene, perylene, fluoranthene, fluorene, and indene; compounds having a π-excess aromatic group such as a cyclopentadiene derivative, a furan derivative, a thiophene derivative, a pyrrole derivative, a benzofuran derivative, a dibenzothiophene derivative, a dinaphthothienothiophene derivative, an indole derivative, a pyrazoline derivative, a dibenzofuran derivative, a dibenzothiophene derivative, and a carbazole derivative; an aromatic amine derivative, a styrylamine derivative, a benzidine derivative, a porphyrin derivative, a phthalocyanine derivative, and a quinacridone derivative.

Hole Blocking Layer

The hole blocking layer is provided in order to inhibit a dark current generated by injecting a hole from one electrode into the photoelectric conversion layer when a bias voltage is applied between the two electrodes. The hole blocking layer also has a function of electron transportation for transporting an electron generated by charge separation in the photoelectric conversion layer toward the electrode. A single layer or multiple layers of the hole blocking layer can be disposed as necessary. For the hole blocking layer, the N-type organic semiconductor material having the electron transportability can be used. The N-type organic semiconductor material may be any material having the electron transportability, and examples thereof include: polycyclic aromatic multivalent carboxylic anhydride or imidized products thereof, such as naphthalenetetracarboxylic diimide and perylenetetracarboxylic diimide; fullerenes, such as C60 and C70; azole derivatives, such as imidazole, triazole, thiadiazole, oxazole, oxadiazole, and triazole; a tris(8-quinolinolate)aluminum (III) derivative, a phosphine oxide derivative, a nitro-substituted fluorene derivative, a diphenylquinone derivative, a thiopyran dioxide derivative, a carbodiimide, a fluorenylidene methane derivative, an anthraquinodimethane derivative and an anthrone derivative, a bipyridine derivative, a quinoline derivative, and an indolocarbazole derivative. Two or more kinds selected from the N-type organic semiconductor materials may be mixed to use.

A method for producing a film of each layer in producing the photoelectric conversion element for imaging of the present invention is not particularly limited. The photoelectric conversion element may be produced by any one of dry process and wet process.

EXAMPLES

Hereinafter, the present invention will be described in more detail with Examples, but the present invention is not limited to these Examples.

Calculation Example

Calculation of HOMO and LUMO Values

Calculated were HOMO and LUMO of the above compounds W1, W2, W3, W4, W5, Wd1, Wd2, Y1, U1, U2, U3, Z1, X1, G1, and Hd1. The calculation was performed by using a density functional theory (DFT), using Gaussian as a calculation program, and with structural optimization calculation of a density functional calculation B3LYP/6-31G (d). Table 1 shows the results. It can be mentioned that any of the materials for the photoelectric conversion element for imaging of the present invention has preferable HOMO and LUMO values.

TABLE 1

| Compound | HOMO [eV] | LUMO [eV] | Compound | HOMO [eV] | LUMO [eV] |
|---|---|---|---|---|---|
| W1 | −5.3 | −1.9 | U1 | −4.8 | −1.1 |
| W2 | −5.1 | −1.9 | U2 | −5.1 | −1.9 |
| W3 | −5.0 | −2.0 | U21 | −5.1 | −1.9 |
| W4 | −5.3 | −1.9 | Z1 | −5.1 | −1.6 |
| W5 | −5.3 | −1.9 | Z1 | −5.1 | −1.6 |
| W26 | −5.2 | −1.7 | X1 | −5.1 | −1.9 |
| Wd1 | −5.3 | −1.8 | G1 | −5.2 | −1.9 |
| Wd2 | −5.3 | −1.9 | Hd1 | −5.3 | −1.7 |
| Y1 | −5.5 | −1.9 | | | |

Synthesis examples of the compounds Wd2, W4, and U3 will be described below as representative examples. The other compounds were also synthesized by similar methods.

Synthesis Example 1 (Synthesis of Wd2)

[C 22]

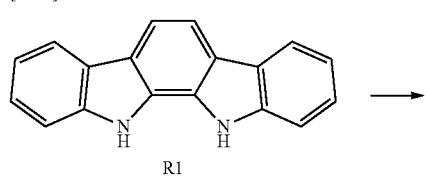

R1

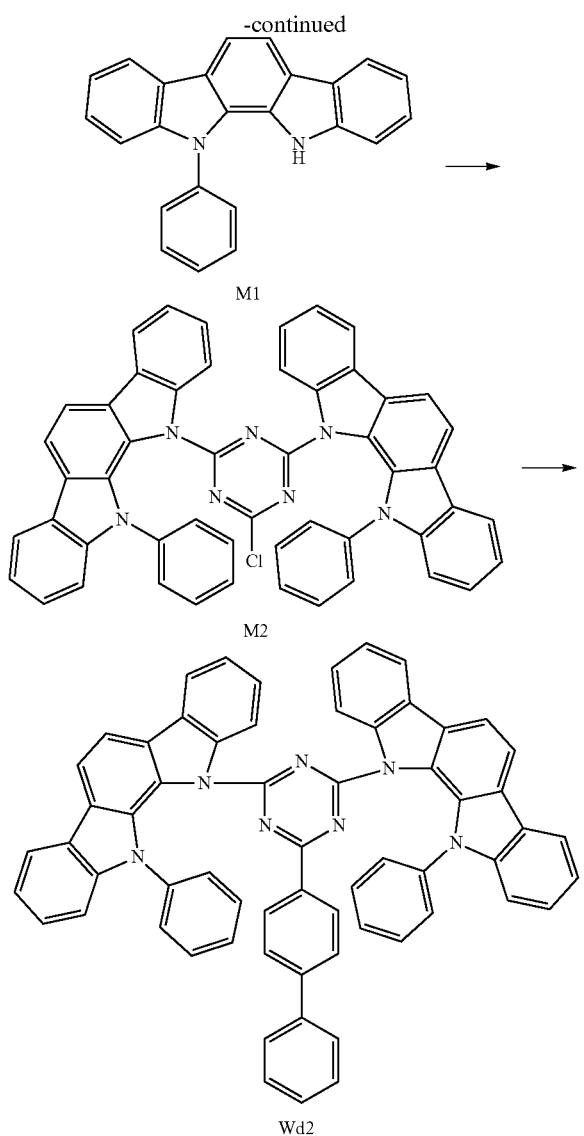

70 ml of dehydrated DMF was added dropwise over 15 minutes. After the dropwise addition, the mixture was continuously stirred for 1 hour. Thereafter, a solution of 3.54 g of cyanuric chloride (19.2 mmol) in 70 ml of dehydrated DMF was added dropwise into the above flask over 15 minutes. After the dropwise addition, the mixture was continuously stirred for 2 hours, then 350 g of water was added, and a precipitate was filtered to obtain M2. The yield was 86%.

Then, M2 obtained in the above (12.9 mmol), 4-biphenylboronic acid (16.4 mmol), tetrakis(triphenylphosphine) palladium (1.3 mmol), 50 ml of ethanol, 100 ml of toulene, and sodium carbonate (47.0 mmol) were dissolved in 50 ml of water, and added into a 1000-ml three-necked flask. The mixture was heated to 85° C. and stirred for 5 hours. The mixture was once cooled to a room temperature, then 100 ml of water and 100 ml of toulene were added, the mixture was stirred, and then an insoluble product was filtered off. The filtrate was transferred into a 1000-ml separatory funnel and separation into an organic layer and an aqueous layer was performed. The organic layer was washed three times with 100 ml of water, and then the obtained organic layer was concentrated under a reduced pressure. The obtained residue was subjected to column chromatography to obtain a compound Wd2 (yellow solid). The yield was 93%. The obtained yellow solid was evaluated by an XRD method but no peak was detected. Thus, this compound was found to be amorphous.

Synthesis Example 2 (Synthesis of W4)

[C 23]

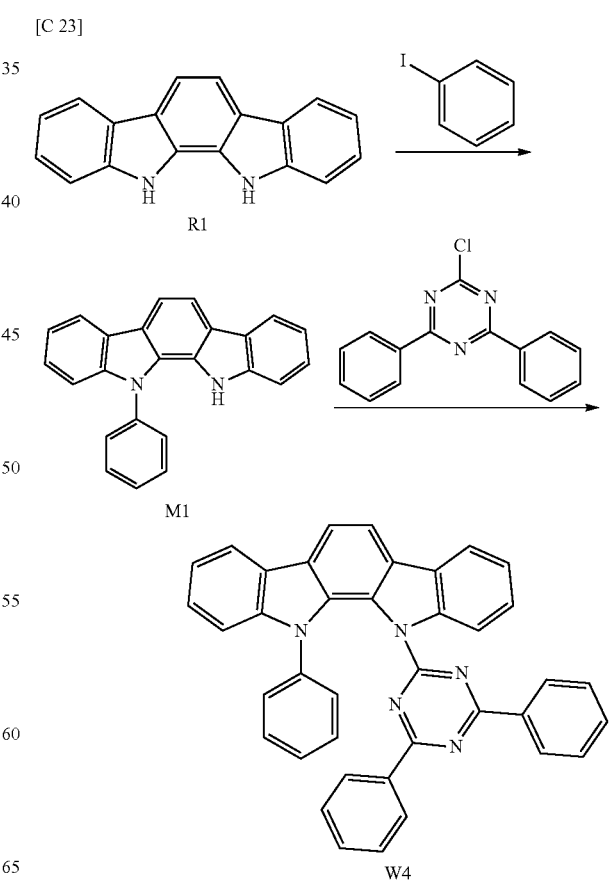

Into a three-necked 2000-ml flask with degassed and nitrogen-replenished, R1 (101.4 mmol), idobenzene (601.4 mmol), copper iodide (287.2 mmol), and potassium carbonate (482.6 mmol) were added, 800 ml of quinoline was added thereinto, and then the mixture was stirred at 190° C. for 72 hours. The mixture was once cooled to a room temperature, and then 500 ml of water and 500 ml of dichloromethane were added to filter a produced yellow precipitate. The filtrate was transferred to a 2000-ml separatory funnel and separation into an organic layer and an aqueous layer was performed. The organic layer was washed three times with 500 ml of water, the obtained organic layer was dehydrated with magnesium sulfate, and then concentrated under a reduced pressure. The obtained residue was purified by column chromatography to obtain M1 (white solid). The yield was 80%.

Then, into a three-necked 500-ml flask with degassed and nitrogen-replenished, 55% sodium hydride (49.5 mmol) was added, 70 ml of dehydrated N,N-dimethylformamide (DMF) was added, and the mixture was stirred under a nitrogen flow. Into this DMF solution, a separately prepared solution of the intermediate 1 obtained in the above (38.3 mmol) in At a room temperature under a nitrogen atmosphere, M1 (71.9 mmol) obtained from R1 by the method of Synthesis Example 1 and sodium hydride (78.8 mmol) were added into DMF (100 ml), and the mixture was stirred. After 30 minutes, diphenylchlorotriazine (79.2 mmol) was added, and the mixture was stirred at a room temperature. After 1 hour, 100 ml of distilled water was added. The precipitate was filtered, recrystallized, and subjected to column chromatography to obtain a compound W4 (yellow crystal). The yield was 90%. The obtained yellow solid was evaluated by an XRD method but no peak was detected. Thus, this compound was found to be amorphous.

Synthesis Example 4 (Synthesis of U3)

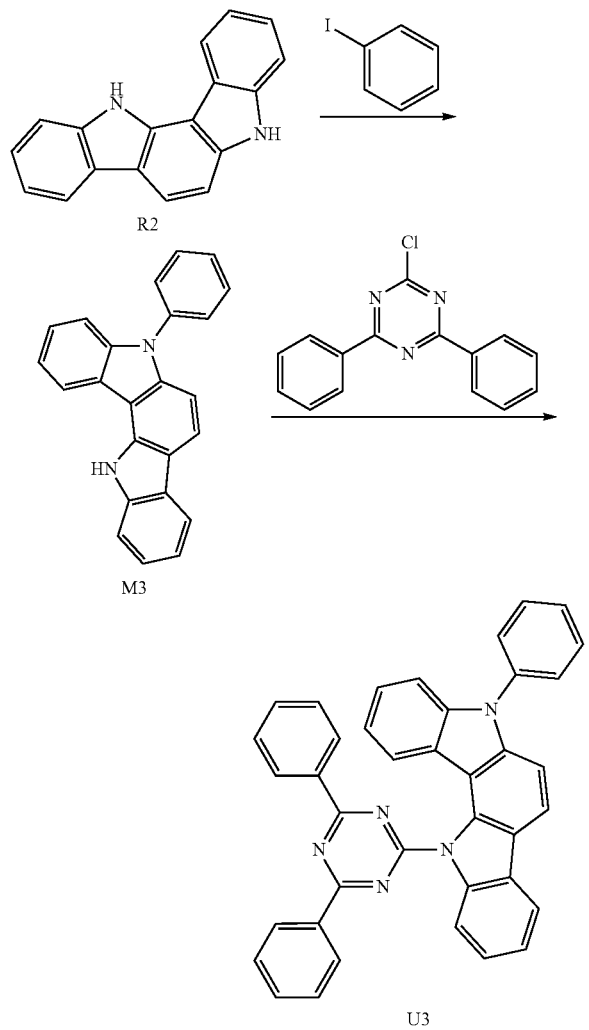

M3 was obtained in the same procedure as in Synthesis Example 1 except that R2 was used instead of R1. The yield was 85%. Then, a compound U3 (yellow crystal) was obtained in the same procedure as in Synthesis Example 2 except that M3 was used instead of M1. The yield was 91%. The obtained yellow solid was evaluated by an XRD method but no peak was detected. Thus, this compound was found to be amorphous.

Example of Physical Properties Evaluation

On a glass substrate on which a transparent electrode composed of ITO with 110 nm in film thickness was formed, the compound W1 was produced to a film as an organic layer by a vacuum deposition method under a condition that a film thickness was approximately 3 μm. Subsequently, charge mobility was measured by a time-of-flight method using an element in which aluminum (Al) was formed with 70 nm in thickness as an electrode. As a result, the hole mobility was $7 \times 10^{-5}$ cm²/Vs.

The hole mobilities were evaluated in the same procedure as above except that W4, Wd1, Y1, and U1 were used instead of the compound W1. Table 2 shows the results.

TABLE 2

| Compound | Hole mobility cm²/Vs | Compound | Hole mobility [cm²/Vs] |
|---|---|---|---|
| W1 | $7 \times 10^{-5}$ | Wd1 | $2 \times 10^{-4}$ |
| W4 | $4 \times 10^{-5}$ | Wd2 | $1 \times 10^{-4}$ |
| W5 | $4 \times 10^{-5}$ | Y1 | $4 \times 10^{-5}$ |
| W26 | $6 \times 10^{-5}$ | U1 | $4 \times 10^{-5}$ |
|  |  | U21 | $9 \times 10^{-5}$ |

Example 1

On a glass substrate on which an electrode composed of ITO with 70 nm in film thickness was formed, a 100-nm film of the compound W1 was formed with a vacuum degree of $4.0 \times 10^{-5}$ Pa as an electron blocking layer. Then, a 100-nm thin film of quinacridone was formed as a photoelectric conversion layer. Finally, a 70-nm aluminum film was formed as an electrode to produce a photoelectric conversion element.

A current in a dark place was $5.3 \times 10^{-12}$ A/cm² with the electrodes of ITO and aluminum and with applying a voltage of 2 V. When a voltage of 2 V was applied and the ITO electrode side was irradiated with light with an LED adjusted to be a irradiation light wavelength of 500 nm and 1.6 μW from a height of 10 cm, a current was $4.3 \times 10^{-6}$ A/cm². A contrast ratio with applying a voltage of 2 V was $8.1 \times 10^{5}$.

Comparative Example 1

On a glass substrate on which an electrode composed of ITO with 70 nm in film thickness was formed, a 100-nm film of quinacridone was formed with a vacuum degree of $4.0 \times 10^{-5}$ Pa as a photoelectric conversion layer. Finally, a 70-nm aluminum film was formed as an electrode to produce a photoelectric conversion element. A current in a dark place was $6.3 \times 10^{-8}$ A/cm² with the electrodes of ITO and aluminum and with applying a voltage of 2 V. When a voltage of 2 V was applied and the ITO electrode side was irradiated with light with an LED adjusted to be an irradiation light wavelength of 500 nm and 1.6 μW from a height of 10 cm, a current was $8.6 \times 10^{-6}$ A/cm². A contrast ratio was $1.4 \times 10 2$ with applying a voltage of 2 V.

The results of Example 1 and Comparative Example 1 were also shown in Table 3.

TABLE 3

| | Compound | Dark current [A/cm$^2$] | Bright current [A/cm$^2$] | Contrast ratio |
|---|---|---|---|---|
| Example 1 | W1 | $5.3 \times 10^{-12}$ | $4.3 \times 10^{-6}$ | $8.1 \times 10^5$ |
| Comparative Example 1 | — | $6.3 \times 10^{-8}$ | $8.6 \times 10^{-6}$ | $1.4 \times 10^2$ |

Example 2

On a glass substrate on which an electrode composed of ITO with 70 nm in film thickness was formed, a 10-nm film of the compound W1 was formed with a vacuum degree of $4.0 \times 10^{-5}$ Pa as an electron blocking layer. Then, 2Ph-BTBT, F6-SubPc-OC6F5, and fullerene (C60) were co-deposited at a deposition rate ratio of 4:4:2 with 200 nm to form a film. Subsequently, 10-nm of dpy-NDI was deposited to form a hole blocking layer. Finally, an aluminum film was formed with 70 nm in thickness as an electrode to produce a photoelectric conversion element. A current in a dark place (dark current) was $6.9 \times 10^{-10}$ A/cm$^2$ with the electrodes of ITO and aluminum and with applying a voltage of 2.6 V. When a voltage of 2.6 V was applied and the ITO electrode side was irradiated with light with an LED adjusted to be a irradiation light wavelength of 500 nm and 1.6 μW from a heights of 10 cm, a current (bright current) was $3.0 \times 10^{-7}$ A/cm$^2$. A contrast ratio was $4.4 \times 10^2$ with applying a voltage of 2.6 V.

[C 25]

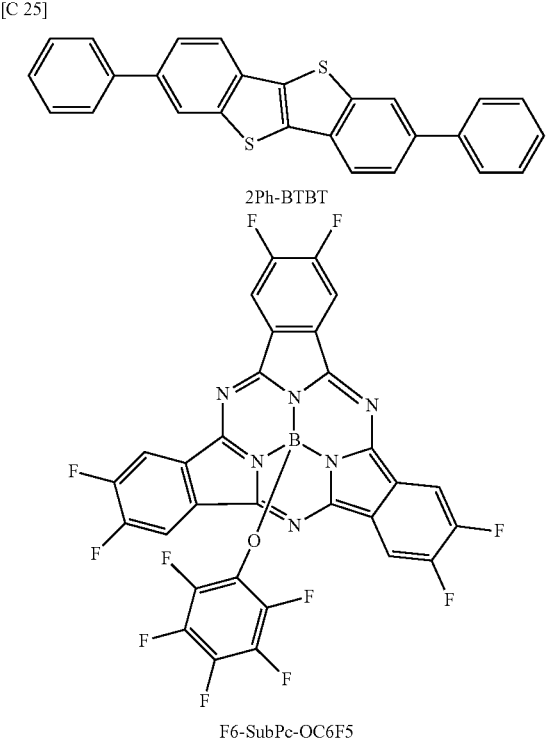

2Ph-BTBT

F6-SubPc-OC6F5

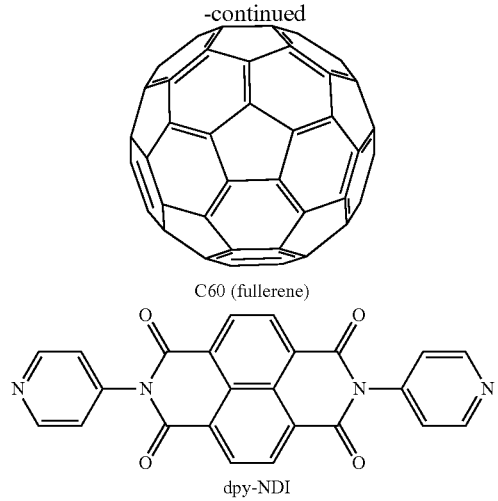

C60 (fullerene)

dpy-NDI

Examples 3 to 5 and Comparative Example 2

Photoelectric conversion elements were produced in the same manner as in Example 2 except that compounds shown in the following Table 4 were used for the electron blocking layer. CzBDF used in Comparative Example 2 is a material disclosed in prior Patent Literature 3.

TABLE 4

[C 26]

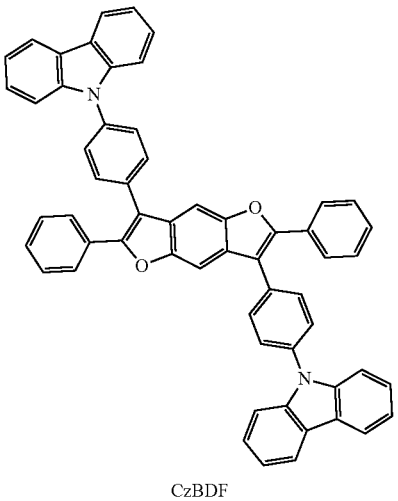 [SMILES: c1ccc(-c2oc3cc4c(-c5ccc(-n6c7ccccc7c7ccccc76)cc5)c(-c5ccccc5)oc4cc3c2-c2ccc(-n3c4ccccc4c4ccccc43)cc2)cc1]

CzBDF

| | Compound | Dark current [A/cm$^2$] | Bright current [A/cm$^2$] | Contrast ratio |
|---|---|---|---|---|
| Example 2 | W1 | $6.9 \times 10^{-10}$ | $3.0 \times 10^{-7}$ | $4.4 \times 10^2$ |
| Example 3 | W26 | $3.2 \times 10^{-10}$ | $3.2 \times 10^{-7}$ | $1.0 \times 10^3$ |
| Example 4 | Wd2 | $6.8 \times 10^{-10}$ | $2.9 \times 10^{-7}$ | $4.3 \times 10^2$ |
| Example 5 | U21 | $5.7 \times 10^{-10}$ | $3.1 \times 10^{-7}$ | $5.4 \times 10^2$ |
| Comparative Example 2 | CzBDF | $1.6 \times 10^{-9}$ | $1.4 \times 10^{-7}$ | $8.4 \times 10^1$ |

INDUSTRIAL APPLICABILITY

The present invention is useful for the material for a photoelectric conversion element for a photoelectric conversion film-stacked imaging device.

REFERENCE SIGNS LIST

1 Electrode
2 Hole blocking layer
3 Photoelectric conversion layer
4 Electron blocking layer
5 Electrode
6 Substrate

The invention claimed is:
1. A material for a photoelectric conversion element for imaging, the material being a compound having a structure of the following general formula (1):

wherein L each independently represents a single bond, a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, or a substituted or unsubstituted linked aromatic group in which two to six of any one or more of the aromatic hydrocarbon group or the aromatic heterocyclic group are linked;
"a" represents the number of substitutions, and represents an integer of 1 to 6;
$Ar^1$ each independently represents a group represented by the following formula (2); and
$Ar^2$ each independently represents a substituted or unsubstituted aromatic heterocyclic group having 3 to 30 carbon atoms and containing a nitrogen-containing six-membered cyclic structure, or a substituted or unsubstituted linked aromatic group which contains at least one of the aromatic heterocyclic group and in which two to seven of any one or more of the aromatic heterocyclic group or an aromatic hydrocarbon group having 6 to 30 carbon atoms are linked, provided that a group bonded to L is the aromatic heterocyclic group,

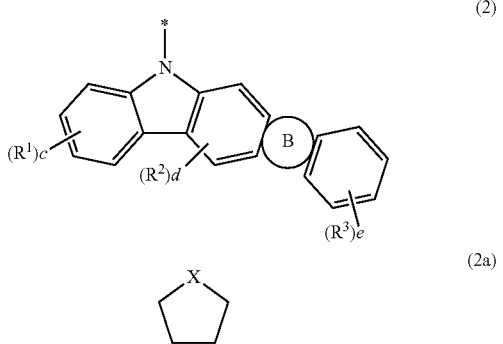

wherein ring B represents a heterocyclic ring represented by the formula (2a) and fused with an adjacent ring at any position; "*" in the formula (2) represents a bonding position to L in the formula (1); and X represents O, S, or N—$Ar^3$;
$Ar^3$ each independently represents a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, a substituted or unsubstituted linked aromatic group in which two to six of any one or more of the aromatic hydrocarbon group or the aromatic heterocyclic group are linked, or L-$Ar^2$;
$R^1$, $R^2$, and $R^3$ represent a substituent, and each independently represent an alkyl group having 1 to 20 carbon atoms, an alkenyl group having 1 to 20 carbon atoms, a substituted or unsubstituted aromatic hydrocarbon group having 6 to 30 carbon atoms, a substituted or unsubstituted aromatic heterocyclic group having 4 to 30 carbon atoms and containing a five-membered heterocyclic structure, or a substituted or unsubstituted linked aromatic group in which two to six of any one or more of the aromatic hydrocarbon group or the aromatic heterocyclic group are linked; and $R^1$, $R^2$, and $R^3$ are optionally bonded to any adjacent substituent to form a ring or form a fused ring with an adjacent ring; and
"c" represents an integer of 0 to 4, "d" represents an integer of 0 to 2, and "e" represents an integer of 0 to 4.

2. The material for a photoelectric conversion element for imaging according to claim 1, wherein $Ar^2$ contains at least one substituted or unsubstituted azine skeleton.

3. The material for a photoelectric conversion element for imaging according to claim 2, wherein $Ar^2$ contains at least one substituted or unsubstituted pyridine, pyrimidine, or triazine skeleton.

4. The material for a photoelectric conversion element for imaging according to claim 3, wherein $Ar^2$ contains at least one substituted or unsubstituted triazine skeleton.

5. The material for a photoelectric conversion element for imaging according to claim 1, wherein an energy level of highest occupied molecular orbital (HOMO) obtained by structural optimization calculation with a density functional calculation B3LYP/6-31G(d) is −4.5 eV or lower.

6. The material for a photoelectric conversion element for imaging according to claim 5, wherein an energy level of lowest unoccupied molecular orbital (LUMO) obtained by structural optimization calculation with a density functional calculation B3LYP/6-31G(d) is −2.5 eV or higher.

7. The material for a photoelectric conversion element for imaging according to claim 1, wherein the material has a hole mobility of $1×10^{−6}$ cm$^2$/Vs or more.

8. The material for a photoelectric conversion element for imaging according to claim 1, wherein when any one of L, the substituent in $Ar^2$, $Ar^3$, the substituent in $Ar^3$, $R^1$, $R^2$, and $R^3$ represents the aromatic heterocyclic group having 4 to 30 carbon atoms and containing a five-membered heterocyclic structure, the five-membered heterocyclic structure is a pyrrole ring, a furan ring, or a thiophene ring.

9. The material for a photoelectric conversion element for imaging according to claim 1, wherein the material for a photoelectric conversion element is amorphous.

10. The material for a photoelectric conversion element for imaging according to claim 1, wherein the material is used as a hole transport material.

11. A photoelectric conversion element for imaging, comprising a photoelectric conversion layer and an electron blocking layer between two electrodes, wherein at least one layer of the photoelectric conversion layer or the electron blocking layer contains the material for a photoelectric conversion element for imaging according to claim 1.

12. The photoelectric conversion element for imaging according to claim 11, wherein the photoelectric conversion layer contains an electron transport material.

13. The photoelectric conversion element for imaging according to claim 11, wherein the electron blocking layer contains the material for a photoelectric conversion element for imaging.

* * * * *